(12) United States Patent
Bunney, Jr. et al.

(10) Patent No.: US 7,341,832 B2
(45) Date of Patent: Mar. 11, 2008

(54) GENES INVOLVED IN NEUROPSYCHIATRIC DISORDERS

(75) Inventors: William E. Bunney, Jr., Laguna Beach, CA (US); Edward G. Jones, Winters, CA (US); Margherita Molnar, Davis, CA (US)

(73) Assignee: The Board of Trustees of the Leland Stanford Junior University, Palo Alto, CA (US), on behalf of the Pritzker Neuropsychiatric Research Consortium ( * ) Notice: Subject to any disclaimer, the term of this patent is extended or adjusted under 35 U.S.C. 154(b) by 177 days.

(21) Appl. No.: 10/649,400

(22) Filed: Aug. 26, 2003

(65) Prior Publication Data

US 2004/0110198 A1    Jun. 10, 2004

Related U.S. Application Data

(60) Provisional application No. 60/451,306, filed on Feb. 27, 2003, provisional application No. 60/406,879, filed on Aug. 28, 2002.

(51) Int. Cl.
*C12Q 1/68* (2006.01)
*A61K 49/00* (2006.01)

(52) U.S. Cl. .......................................... 435/6; 424/9.1

(58) Field of Classification Search ...................... None
See application file for complete search history.

(56) References Cited

OTHER PUBLICATIONS

Iino et al. (2003) Int. J. Legal Med. 117, 153-159.*
Pleines et al. (2001). J. Neurotrauma. 18, 491-498.*
Molnar et al. (2003). Biol. Psych. 39-47.*
Bulfone et al (1998). Neuron. 21, 1273-1282.*
Hevner et al. Neuron. 29, 353-366.*
Xing et al (2002). Clinical Neuroscience and Neuropathology. 13, 501-505.*
Hevner et al. Neuron. 29, 353-366, 2001.*
Margherita Molnar et al., *mRNA Expression Patterns and Distribution of White Matter Neurons in Dorsolateral Prefrontal Cortex of Depressed Patients Differ from Those in Schizophrenia Patients*, Biol. Psychiatry, 2003:53:39-47.
Torrey, et al.; The Stanley Foundation brain collection and Neuropathology Consortium; Schizophrenia Research 44 (2000); 151-155.
Li, et al.; Systematic changes in gene expression in postmortem human brains associated with tissue pH and terminal medical conditions; *Human Molecular Genetics*; (2004) vol. 13, No. 6; 609-616.
Evans, et al.; Dysregulation of the fibroblast growth factor system in major depression; *PNAS*; (2004) vol. 101, 15506-15511.
Choudary, et al.; Altered cortical glumamatergic and GABAergic signal transmission with glial involvement in depression; *PNAS*; (2005) vol. 102, 15653-15658.
Novak, et al.; Increased Expression of Calcium Calmodulin-Depdendent Protein Kinase IIβ in Frontal Cortex in Schizophrenia and Depression; *SYNAPSE* (2006) 59:61-68.
Iwamoto, et al.; Gene Expression Profiling in Schizophrenia and Related Mental Disorders; *The Neuroscientist*; (2006) vol. 12, 349-361.
Bunney, et al.; Microarray Technology: A Review of New Strategies to Discover Candidate Vulnerability Genes in Psychiatric Disorders; *Am J Psychiatry*; (2003) 160:4, 657-666.
Atz, et al.; Methodological considerations for gene expression profiling of human brain; *Journal of Neuroscience Methods*; (2007).
Mexal, et al.; Brain pH has a significant impact on human postmortem hippocampal gene expression profiles; *Brain Research*; (2006) 1106: 1-11.
Tomita et al.; Effect of Agonal and Postmortem Factors on Gene Expression Profile: Quality Control in Microarray Analyses of Postmortem Human Brain; *Biol Psychiatry*; (2004) 55:346-352.

* cited by examiner

*Primary Examiner*—Christina Chan
*Assistant Examiner*—Steve Standley
(74) *Attorney, Agent, or Firm*—Townsend and Townsend and Crew LLP

(57) ABSTRACT

The present invention provides methods for diagnosing mental disorders. The invention also provides methods of identifying modulators of mental disorders as well as methods of using these modulators to treat patients suffering from mental disorders.

5 Claims, 9 Drawing Sheets

FIGURE 1

SEQ ID NO:1  Human CAMKII-α nucleic acid sequence

The sequence in bold and italic was used for transcribing the riboprobe in Example 1.

```
        ttcaggatgg ctaccatcac ctgcacccgc ttcacggaag agtaccagct cttcgaggaa
   61   ttgggcaagg gagccttctc ggtggtgcga aggtgtgtga aggtgctggc tggccaggag
  121   tatgctgcca agatcatcaa cacaaagaag ctgtcagcca gagaccatca gaagctggag
  181   cgtgaagccc gcatctgccg cctgctgaag cacccaaca tcgtccgact acatgacagc
  241   atctcagagg agggacacca ctacctgatc ttcgacctgg tcactggtgg ggaactgttt
  301   gaagatatcg tggcccggga gtattacagt gaggcggatg ccagtcactg tatccagcag
  361   atcctggagg ctgtgctgca ctgccaccag atgggggtgg tgcaccggga cctgaagcct
  421   gagaatctgt tgctggcctc caagctcaag ggtgccgcag tgaagctggc agactttggc
  481   ctggccatag aggtggaggg ggagcagcag gcatggtttg ggtttgcagg gactcctgga
  541   tatctctccc cagaagtgct gcggaaggac ccgtacggga agcctgtgga cctgtgggct
  601   tgtggggtca tcctgtacat cctgctggtt gggtaccccc cgttctggga tgaggaccag
  661   caccgcctgt accagcagat caaagccggc gcctatgatt tcccatcgcc ggaatgggac
  721   actgtcaccc cggaagccaa ggatctgatc aataagatgc tgaccattaa cccatccaaa
  781   cgcatcacag ctgccgaagc ccttaagcac ccctggatct cgcaccgctc caccgtggca
  841   tcctgcatgc acagacagga gaccgtggac tgcctgaaga gttcaatgc caggaggaaa
  901   ctgaagggag ccattctcac cacgatgctg gccaccagga acttctccgg agggaagagt
  961   gggggaaaca agaagagcga tggtgtgaag aaaagaaagt ccagttccag cgttcagtta
 1021   atggaatcct cagagagcac caacaccacc atcgaggatg aagacaccaa agtgcggaaa
 1081   caggaaatta taaaagtgac agagcagctg attgaagcca taagcaatgg aggttttgag
 1141   tcctacacga agatgtgcga ccctggcatg acagccttcg aacctgaggc cctggggaac
 1201   ctggttgagg gcctggactt ccatcgattc tattttgaaa acctgtggtc ccggaacagc
 1261   aagcccgtgc acaccaccat cctgaatccc cacatccacc tgatgggcga cgagtcagcc
 1321   tgcatcgcct acatccgcat cacgcagtac ctggacgctg gcggcatccc acgcaccgcc
 1381   cagtcggagg agaccgtgt ctggcaccgc cgggacggca atggcagat cgtccacttc
 1441   cacagatctg gggcgccctc cgtcctgccc cattgaagga ccaggccagg gtcaa
```

FIGURE 2

SEQ ID NO:2 Human CAMKII-α Amino acid sequence

```
1    MATITCTRFT EEYQLFEELG KGAFSVVRRC VKVLAGQEYA AKIINTKKLS ARDHQKLERE
61   ARICRLLKHP NIVRLHDSIS EEGHHYLIFD LVTGGELFED IVAREYYSEA DASHCIQQIL
121  EAVLHCHQMG VVHRDLKPEN LLLASKLKGA AVKLADFGLA IEVEGEQQAW FGFAGTPGYL
181  SPEVLRKDPY GKPVDLWACG VILYILLVGY PPFWDEDQHR LYQQIKAGAY DFPSPEWDTV
241  TPEAKDLINK MLTINPSKRI TAAEALKHPW ISHRSTVASC MHRQETVDCL KKFNARRKLK
301  GAILTTMLAT RNFSGGKSGG NKKSDGVKKR KSSSSVQLME SSESTNTTIE DEDTKVRKQE
361  IIKVTEQLIE AISNGGFESY TKMCDPGMTA FEPEALGNLV EGLDFHRFYF ENLWSRNSKP
421  VHTTILNPHI HLMGDESACI AYIRITQYLD AGGIPRTAQS EETRVWHRRD GKWQIVHFHR
481  SGAPSVLPH
```

FIGURE 3

SEQ ID NO:3: Human TBR1 Nucleic acid sequence (NCBI Accession NM 006593)

The sequence in bold and italic was used for transcribing the riboprobe in Example 1.

```
   1  caggtgatta tcctaattaa tgtctatcta attaaattac tgtcagcagc taaccaatgg
  61  caggagccgt ttcatcggct gcacaagcag caagatcaaa agtgagcctt ttctgattgc
 121  tgcatagtgt caattggcca atctcttctc ccagggaaaa aaaaagtaa atcaaacctt
 181  tgagaagcat ttgctggttg aagtgctttc tgtctagtga gggggtctgt ggatttctag
 241  tttatgataa ataggacttt aaaaaccagg gacgggaggg cgagtgttca ggttctagag
 301  ctatgcagct ggagcactgc ctttctcctt ctatcatgct ctccaagaaa tttctcaatg
 361  tgagcagcag ctacccacat tcaggcggat ccgagcttgt cttgcacgat catcccatta
 421  tctcgaccac tgacaacctg gagagaagtt cacctttgaa aaaattacc aggggatga
 481  cgaatcagtc agatacagac aattttcctg actccaagga ctcaccaggg gacgtccaga
 541  gaagtaaact ctctcctgtc ttggacgggg tctctgagct tcgtcacagt ttcgatggct
 601  ctgctgcaga tcgctacctc ctctctcagt ccagccagcc acagtctgcg gccactgctc
 661  ccagtgccat gttcccgtac cccggccagc acggaccggc gcacccgcc ttctccatcg
 721  gcagccctag ccgctacatg gccaccacc cggtcatcac caacggagcc tacaacagcc
 781  tcctgtccaa ctcctcgccg cagggatacc ccacggccgg ctacccctac ccacagcagt
 841  acggccactc ctaccaagga gctccgttct accagttctc ctcacccag ccggggctgg
 901  tgcccggcaa agcacaggtg tacctgtgca acaggcccct ttggctgaaa tttcaccggc
 961  accaaacgga gatgatcatc accaaacagg gaaggcgcat gtttcctttt ttaagtttta
1021  acatttctgg tctcgatccc acggctcatt acaatatttt tgtggatgtg attttggcgg
1081  atcccaatca ctggaggttt caaggaggca aatgggttcc ttgcggcaaa gcggacacca
1141  atgtgcaagg aaatcgggtc tatatgcatc cggattcccc caacagtggg gctcactgga
1201  tgcgccaaga aatctctttt ggaaaattaa aacttacgaa caacaaagga gcttcaaata
1261  acaatgggca gatggtggtt ttacagtcct tgcacaagta ccagccccgc ctgcatgtgg
1321  tggaagtgaa cgaggacggc acggaggaca ctagccagcc cggccgcgtg cagacgttca
1381  ctttccctga gactcagttc atcgccgtca ccgcctacca gaacacggat attacacaac
1441  tgaaaataga tcacaaccct tttgcaaaag gatttcggga taattatgac acgatctaca
1501  ccggctgtga catggaccgc ctgacccct cgcccaacga ctcgccgcgc tgcagatcg
1561  tgcccggggc ccgctacgcc atggccggct ctttcctgca ggaccagttc gtgagcaact
1621  acgccaaggc ccgcttccac ccgggcgcgg gcgcgggccc cggccgggt acggaccgca
1681  gcgtgccgca caccaacggg ctgctgtcgc cgcagcaggc cgaggacccg ggcgcgccct
1741  cgccgcaacg ctggtttgtg acgccggcca caaccggct ggacttcgcg gcctcggcct
1801  atgacacggc cacggacttc gcgggcaacg cggccacgct gctctcttac gcggcggcgg
1861  gcgtgaaggc gctgccgctg caggctgcag gctgcactgg ccgcccgctc ggctactacg
1921  ccgacccgtc gggctggggc gcccgcagtc ccccgcagta ctgcggcacc aagtcgggct
```

FIGURE 3 continued

```
1981 cggtgctgcc ctgctggccc aacagcgccg cggccgccgc gcgcatggcc ggcgccaatc
2041 cctacctggg cgaggaggcc gagggcctgg ccgccgagcg ctcgccgctg ccgcccggcg
2101 ccgccgagga cgccaagccc aaggacctgt ccgattccag ctggatcgag acgccctcct
2161 cgatcaagtc catcgactcc agcgactcgg ggatttacga gcaggccaag cggaggcgga
2221 tctcgccggc cgacacgccc gtgtccgaga gttcgtcccc gctcaagagc gaggtgctgg
2281 cccagcggga ctgcgagaag aactgcgcca aggacattag cggctactat ggcttctact
2341 cgcacagcta ggccgcccct gcccgccgg ccccgccgcg gcccggaccc ccagccagcc
2401 cctcacagct cttcccagc tccgcctccc cacactcctc cttgcgcacc cactcatttt
2461 atttgaccct cgatggccgt ctgcagcgaa taagtgcagg tctccgagcg tgatttaac
2521 cttttttgca cagcagtctc tgcaattagc tcaccgacct tcaactttgc tgtaaacctt
2581 ttggttttcc tacttactct tcttctgtgg agttatcctc ctacaattcc cctcccctc
2641 gtctttctct tacctcctac ttctcttct tgtaatgaaa ctcttcacct ttaggagacc
2701 tgggcagtcc tgtcaggcag cagcgattcc gacccgccaa gtctcggcct ccacattaac
2761 cataggatgt tgactctaga acctggaccc acccagcgcg tcctttctta tccccgagtg
2821 gatggatgga tggatggatg gtagggatgt taataatttt agtggaacaa agcctgtgaa
2881 atgattgtac atagtgttaa tttattgtaa cgaatggcta gttttattc tcgtcaaggc
2941 acaaaaccag ttcatgctta accttttttt cctttccttt ctttgctttt ctttctctcc
3001 tctcatactt tctcttctct ctcttttaat tttcttgtga gataatattc taagaggctc
3061 tagaaacatg aaatactcag tagtgatggg tttcccactt ctcctcaatc cgttgcatga
3121 aataattact atgtgcccta atgcacacaa atagctaagg agaatccacc caaacacctt
3181 taaagg
```

FIGURE 4

SEQ ID NO:4 Human TBR1 Amino acid sequence

```
1   MQLEHCLSPS IMLSKKFLNV SSSYPHSGGS ELVLHDHPII STTDNLERSS PLKKITRGMT
61  NQSDTDNFPD SKDSPGDVQR SKLSPVLDGV SELRHSFDGS AADRYLLSQS SQPQSAATAP
121 SAMFPYPGQH GPAHPAFSIG SPSRYMAHHP VITNGAYNSL LSNSSPQGYP TAGYPYPQQY
181 GHSYQGAPFY QFSSTQPGLV PGKAQVYLCN RPLWLKFHRH QTEMIITKQG RRMFPFLSFN
241 ISGLDPTAHY NIFVDVILAD PNHWRFQGGK WVPCGKADTN VQGNRVYMHP DSPNTGAHWM
301 RQEISFGKLK LTNNKGASNN NGQMVVLQSL HKYQPRLHVV EVNEDGTEDT SQPGRVQTFT
361 FPETQFIAVT AYQNTDITQL KIDHNPFAKG FRDNYDTIYT GCDMDRLTPS PNDSPRSQIV
421 PGARYAMAGS FLQDQFVSNY AKARFHPGAG AGPGPGTDRS VPHTNGLLSP QQAEDPGAPS
481 PQRWFVTPAN NRLDFAASAY DTATDFAGNA ATLLSYAAAG VKALPLQAAG CTGRPLGYYA
541 DPSGWGARSP PQYCGTKSGS VLPCWPNSAA AAARMAGANP YLGEEAEGLA AERSPLPPGA
601 AEDAKPKDLS DSSWIETPSS IKSIDSSDSG IYEQAKRRRI SPADTPVSES SSPLKSEVLA
661 QRDCEKNCAK DISGYYGFYS HS
```

CAMKII-α mRNA Levels in 6 Layers of Dorsolateral Prefrontal Cortex (DLPFC in the Brains of Bipolar patients and Normal Controls TBR1 mRNA Levels in 6 Layers of Dorsolateral Prefrontal Cortex (DLPFC in the Brains of Bipolar patients and Normal Controls

Figure 8

CAMK I nucleotide and amino acid sequence

SEQ ID NO:5

```
   1 ggagagagcc gccgagccga gccgagcccc agctccagca agagcgcggg cgggtggccc
  61 aggcacgcag cggtgaggac cgcggccaca gctcggcgcc aaccaccgcg ggcctcccag
 121 ccagccccgc ggcggggcag ccgcaggagc cctggctgtg gtcgggggc agtgggccat
 181 gctgggggca gtggaaggcc ccaggtggaa gcaggcggag gacattagag acatctacga
 241 cttccgagat gttctgggca cgggggcctt ctcggaggtg atcctggcag aagataagag
 301 gacgcagaag ctggtggcca tcaaatgcat tgccaaggag gccctggagg gcaaggaagg
 361 cagcatggag aatgagattg ctgtcctgca caagatcaag caccccaaca ttgtagccct
 421 ggatgacatc tatgagagtg ggggccacct ctacctcatc atgcagctgg tgtcgggtgg
 481 ggagctcttt gaccgtattg tggaaaaagg cttctacacg gagcgggacg ccagccgcct
 541 catcttccag gtgctggatg ctgtgaaata cctgcatgac ctgggcattg tacaccggga
 601 tctcaagcca gagaatctgc tgtactacag cctggatgaa gactccaaaa tcatgatctc
 661 cgactttggc ctctccaaga tggaggaccc gggcagtgtg ctctccaccg cctgtggaac
 721 tccgggatac gtggcccctg aagtcctggc ccagaagccc tacagcaagg ctgtggattg
 781 ctggtccata ggtgtcatcg cctacatctt gctctgcggt tacccctcct tctatgacga
 841 gaatgatgcc aaactctttg aacagatttt gaaggccgag tacgagtttg actctcctta
 901 ctgggacgac atctctgact ctgccaaaga tttcatccgg cacttgatgg agaaggaccc
 961 agagaaaaga ttcacctgtg agcaggcctt gcagcaccca tggattgcag gagatacagc
1021 tctagataag aatatccacc agtcggtgag tgagcagatc aagaagaact ttgccaagag
1081 caagtggaag caagccttca atgccacggc tgtggtgcgg cacatgagga aactgcagct
1141 gggcaccagc caggaggggc aggggcagac ggcgagccat ggggagctgc tgacaccagt
1201 ggctggggg ccggcagctg gctgttgctg tcgagactgc tgcgtggagc cgggcacaga
1261 actgtccccc acactgcccc accagctcta gggccctgga cctcgggtca tgatcctctg
1321 cgtgggaggg cttgggggca gcctgctccc cttccctccc tgaaccggga gtttctctgc
1381 cctgtcccct cctcacctgc ttccctacca ctcctcactg catttccat acaaatgttt
1441 ctattttatt gttccttctt gtaataaagg gaagataaaa ccaaaaaaaa aaaaaaaaa
1501 a
```

SEQ ID NO:6
MLGAVEGPRWKQAEDIRDIYDFRDVLGTGAFSEVILAEDKRTQKLVAIKCIAKEALEGKEGSMENEIAVLHKIKHPN
IVALDDIYESGGHLYLIMQLVSGGELFDRIVEKGFYTERDASRLIFQVLDAVKYLHDLGIVHRDLKPENLLYYSLDE
DSKIMISDFGLSKMEDPGSVLSTACGTPGYVAPEVLAQKPYSKAVDCWSIGVIAYILLCGYPPFYDENDAKLFEQIL
KAEYEFDSPYWDDISDSAKDFIRHLMEKDPEKRFTCEQALQHPWIAGDTALDKNIHQSVSEQIKKNFAKSKWKQAFN
ATAVVRHMRKLQLGTSQEGQGQTASHGELLTPVAGGPAAGCCCRDCCVEPGTELSPTLPHQL"

GENES INVOLVED IN NEUROPSYCHIATRIC DISORDERS

CROSS-REFERENCES TO RELATED APPLICATIONS

The present application claims priority to U.S. Ser. No. 60/451,306, filed Feb. 27, 2003, and U.S. Ser. No. 60/406,879, filed Aug. 28, 2002, each herein incorporated by reference in their entirety.

STATEMENT AS TO RIGHTS TO INVENTIONS MADE UNDER FEDERALLY SPONSORED RESEARCH AND DEVELOPMENT

This invention was made with government support under NIH grants MH54844 and MH60398. The Government has certain rights in this invention.

BACKGROUND OF THE INVENTION

While it has been hypothesized that mental illness, including mood disorders such as major depression and bipolar disorder as well as psychotic disorders such as psychosis and schizophrenia, may have genetic roots, little progress has been made in identifying gene sequences and gene products that play a role in causing these disorders, as is true for many diseases with a complex genetic origin (see, e.g., Burmeister, *Biol. Psychiatry* 45:522-532 (1999)). Relying on the discovery that certain genes expressed in particular brain pathways and regions are likely involved in the development of mental illness, the present invention provides methods for diagnosis and treatment of mental illness, as well as methods for identifying compounds effective in treating mental illness.

BRIEF SUMMARY OF THE INVENTION

The present invention reveals increased mRNA levels of two genes specifically expressed in the central nervous system, α-type II calcium/calmodulin dependent protein kinase (CAMKII-α) and TBR1, in the brains of patients suffering from mental disorders, such as bipolar disorder and schizophrenia, in comparison with normal control subjects. In addition, the gene CAMKI has altered expression in patients suffering from mental disorders. This invention thus provides methods for determining whether a subject has or is predisposed for a mental disorder. In some embodiments, the methods comprise the steps of: (i) obtaining a biological sample from a subject; (ii) contacting the sample with a reagent that selectively associates with a polynucleotide or polypeptide encoded by a nucleic acid that hybridizes under stringent conditions to a nucleotide sequence of SEQ ID NO:1 or 3; and (iii) detecting the level of reagent that selectively associates with the sample, thereby determining whether the subject has or is predisposed for a mental disorder.

In some embodiments, the reagent is an antibody. In some embodiments, the reagent is a nucleic acid. In some embodiments, the reagent associates with a polynucleotide. In some embodiments, the reagent associates with a polypeptide. In some embodiments, the polynucleotide comprises a nucleotide sequence of SEQ ID NO:1 or 3. In some embodiment, the polypeptide comprises an amino acid sequence of SEQ ID NO:2 or 4. In some embodiments, the level of reagent that associates with the sample is different from a level associated with humans without a mental disorder. In some embodiments, the biological sample is obtained from amniotic fluid. In some embodiments, the mental disorder is a mood disorder or psychosis. In some embodiments, the mood disorder is selected from the group consisting of bipolar disorder and major depression. In some embodiments, the psychosis is schizophrenia.

The invention also provides methods of identifying a compound for treatment of a mental disorder. In some embodiments, the methods comprises the steps of: (i) contacting the compound with a polypeptide, which is encoded by a polynucleotide that hybridizes under stringent conditions to a nucleic acid comprising a nucleotide sequence of SEQ ID NO:1 or 3; and (ii) determining the functional effect of the compound upon the polypeptide, thereby identifying a compound for treatment of a mental disorder.

In some embodiments, the contacting step is performed in vitro. In some embodiment, the polypeptide comprises an amino acid sequence of SEQ ID NO:2 or 4. In some embodiments, the polypeptide is expressed in a cell or biological sample, and the cell or biological sample is contacted with the compound. In some embodiments, the mental disorder is a mood disorder or psychotic disorder. In some embodiments, the mood disorder is selected from the group consisting of bipolar disorder and major depression. In some embodiments, the psychosis is schizophrenia or psychosis. In some embodiments, the methods further comprise administering the compound to an animal and determining the effect on the animal, e.g., an invertebrate, a vertebrate, or a mammal. In some embodiments, the determining step comprises testing the animal's mental function.

In some embodiments, the methods comprise the steps of (i) contacting the compound to a cell, the cell comprising a polynucleotide that hybridizes under stringent conditions to a nucleotide sequence of SEQ ID NO:1 or 3; and (ii) selecting a compound that modulates expression of the polynucleotide, thereby identifying a compound for treatment of a mental disorder. In some embodiments, the polynucleotide comprises a nucleotide sequence of SEQ ID NO:1 or 3. In some embodiment, the expression of the polynucleotide is enhanced. In some embodiments, the expression of the polynucleotide is decreased. In some embodiments, the methods further comprise administering the compound to an animal and determining the effect on the animal. In some embodiments, the determining step comprises testing the animal's mental function. In some embodiments, the mental disorder is a mood disorder or psychosis. In some embodiments, the mood disorder is selected from the group consisting of bipolar disorder and major depression. In some embodiments, the psychosis is schizophrenia.

The invention also provides methods of treating a mental disorder in a subject. In some embodiments, the methods comprise the step of administering to the subject a therapeutically effective amount of a compound identified using the methods described above. In some embodiments, the mental disorder is a mood disorder or psychosis. In some embodiments, the mood disorder is selected from the group consisting of bipolar disorder and major depression. In some embodiments, the psychosis is schizophrenia. In some embodiments, the compound is a polynucleotide. In some embodiments, the polynucleotide hybridizes under stringent conditions to a nucleic acid comprising a nucleotide sequence of SEQ ID NO:1 or 3.

The invention also provides methods of treating mental illness in a subject, comprising the step of administering to the subject a therapeutically effective amount of a polypeptide, which is encoded by a polypeptide that hybridizes under stringent conditions to a nucleic acid of SEQ ID NO:1 or 3. In some embodiments, the polypeptide comprises an amino acid sequence of SEQ ID NO:2 or 4. In some embodiments, the mental illness is a mood disorder or psychosis. In some embodiments, the psychosis is schizophrenia. In some embodiments, the mood disorder is a bipolar disorder or major depression.

The invention also provides methods of treating mental illness in a subject, comprising the step of administering to the subject a therapeutically effective amount of a polypeptide, wherein the polypeptide hybridizes under stringent conditions to a nucleic acid of SEQ ID NO:1 or 3. In some embodiments, the mental illness is a mood disorder or psychosis. In some embodiments, the psychosis is schizophrenia. In some embodiments, the mood disorder is a bipolar disorder or major depression.

Definitions

A "mental disorder" or "mental illness" or "mental disease" refers to mood disorders (e.g., major depression, mania, and bipolar disorders), psychotic disorders or psychosis (e.g., hallucinations, delusions, confused thinking, and schizophrenia), personality disorders, obsessive-compulsive disorders as well as other mental illness with a genetic or biochemical component.

A "mood disorder" refers to disruption of feeling tone or emotional state experienced by an individual for an extensive period of time. Mood disorders include major depression (i.e., unipolar disorder), mania, dysphoria, bipolar disorder, dysthymia, cyclothymia and many others. See, e.g., Diagnostic and Statistical Manual of Mental Disorders, Fourth Edition, (DSM IV).

"Psychosis" refers to a condition that affects the mind, resulting in at least some loss of contact with reality. Symptoms of psychosis include, e.g., hallucinations, change behavior that is not based on reality (e.g., fasting for fear of poison in food, etc.), delusions and the like. See, e.g., DSM IV. Schizophrenia is a type of psychosis.

"Schizophrenia" refers to a mental disorder involving a withdrawal from reality by an individual. Symptoms comprise for at least a part of a month two or more of the following symptoms: delusions (only one symptom is required if a delusion is bizarre, such as being abducted in a space ship from the sun); hallucinations (only one symptom is required if hallucinations are of at least two voices talking to one another or of a voice that keeps up a running commentary on the patient's thoughts or actions); disorganized speech (e.g., frequent derailment or incoherence); grossly disorganized or catatonic behavior; or negative symptoms, i.e., affective flattening, alogia, or avolition. Schizophrenia encompasses disorders such as, e.g., schizoaffective disorders. Diagnosis of schizophrenia is described in, e.g., DSM IV.

"Major depression," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., DSM IV.

"Bipolar disorder" is characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM IV.

The terms "CAMKI," "CAMKII" and "TBR-1" or a nucleic acid encoding refer to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95% 96%, 97%, 98% or 99% or greater amino acid sequence identity, preferably over a region of over a region of at least about 25, 50, 100, 200, 500, 1000, or more amino acids, to a polypeptide encoded by a nucleic acid of SEQ ID NO:1, 3, or 5 or an amino acid sequence of SEQ ID NO:2, 4, or 6; (2) specifically bind to antibodies, e.g., polyclonal antibodies, raised against an immunogen comprising an amino acid sequence of SEQ ID NO:2, 4, or 6, immunogenic fragments thereof, and conservatively modified variants thereof; (3) specifically hybridize under stringent hybridization conditions to a nucleic acid encoding SEQ ID NO:2, 4, or 6, e.g., a nucleic acid sequence of SEQ IN NO:1, 3, or 5 or its complement, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to SEQ ID NO:1, 3, or 5 or its complement. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. A nucleotide and amino acid sequence of human CAMKII-α is found in FIGS. 1 and 2. A nucleotide and amino acid sequence of human TBR-1 is found in FIGS. 3 and 4. A nucleotide and amino acid sequence of human CAMKI is found in FIG. 8. In addition, GenBank Accession numbers for CAMK1 nucleic acid and protein are: NM_003656 (nucleic acid), NP_003647 (protein); and Q14012 (protein). GenBank Accession numbers for TBR-1 nucleic acid and protein are: NM_006593 (nucleic acid) and NP_006584 (protein). GenBank Accession number for CAMKII-α is NM_015981.2 (nucleic acid) and NP_057065.2 (protein). Also encompassed by the invention are all isoforms alpha, beta, delta and gamma for CAMKII, which are known to those of skill in the art and have assigned GenBank Accession numbers.

An "agonist" refers to an agent that binds to a polypeptide or polynucleotide of the invention, stimulates, increases, activates, facilitates, enhances activation, sensitizes or up regulates the activity or expression of a polypeptide or polynucleotide of the invention.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

"Determining the functional effect" refers to assaying for a compound that increases or decreases a parameter that is indirectly or directly under the influence of a polynucleotide or polypeptide of the invention (such as a polynucleotide of SEQ ID NO:1 or 3, or a polypeptide of SEQ ID NO:2 or 4), e.g., measuring physical and chemical or phenotypic effects.

Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; measurement of calcium influx; measurement of protease or RNA helicase activity; measurement of the accumulation of an enzymatic product of a polypeptide of the invention or depletion of an substrate; measurement of changes in protein levels of a polypeptide of the invention; measurement of RNA stability; G-protein binding; GPCR phosphorylation or dephosphorylation; signal transduction, e.g., receptor-ligand interactions, second messenger concentrations (e.g., cAMP, IP3, or intracellular $Ca^{2+}$); identification of downstream or reporter gene expression (CAT, luciferase, β-gal, GFP and the like), e.g., via chemiluminescence, fluorescence, colorimetric reactions, antibody binding, inducible markers, and ligand binding assays.

"Biological sample" includes sections of tissues such as biopsy and autopsy samples, and frozen sections taken for histologic purposes. Such samples include blood, sputum, tissue, lysed cells, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The terms "peptidomimetic" and "mimetic" refer to a synthetic chemical compound that has substantially the same structural and functional characteristics of the polynucleotides, polypeptides, antagonists or agonists of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, *Adv. Drug Res.* 15:29 (1986); Veber and Freidinger *TINS* p. 392 (1985); and Evans et al. *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a CCX CKR, but have one or more peptide linkages optionally replaced by a linkage selected from the group consisting of, e.g., —CH$_2$NH—, —CH$_2$S—, —CH$_2$—CH$_2$—, —CH═CH— (cis and trans), —COCH$_2$—, —CH(OH)CH$_2$—, and —CH$_2$SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or enzymatic activities of a polypeptide or polynucleotide of the invention or inhibiting or increasing the enzymatic activity or expression of a polypeptide or polynucleotide of the invention.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes. Nucleic acids that hybridize to SEQ ID NO:1 or 3 are encompassed by the invention.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrase "a nucleic acid sequence encoding" refers to a nucleic acid that contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual,* Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

One who is "predisposed for a mental disorder" as used herein means a person who has an inclination or a higher likelihood of developing a mental disorder when compared to an average person in the general population.

BRIEF DESCRIPTION OF THE DRAWINGS

FIG. 1 shows the nucleic acid sequence of human CAMKII-α (SEQ ID NO:1). The sequence used in Example 1 to transcribe a CAMKII-α riboprobe is indicated in bold and italic.

FIG. 2 shows the amino acid sequence of human CAMKII-α (SEQ ID NO:2).

FIG. 3 shows the nucleic acid sequence of human TBR1 (SEQ ID NO:3). The sequence used in Example 1 to transcribe a TBR1 riboprobe is indicated in bold and italic.

FIG. 4 shows the amino acid sequence of human TBR1 (SEQ ID NO:4).

FIG. 8 shows the nucleotide (SEQ ID NO:5) and amino acid (SEQ ID NO:6) sequence of CAMKI.

DETAILED DESCRIPTION OF THE INVENTION

I. Introduction

Figure 5:
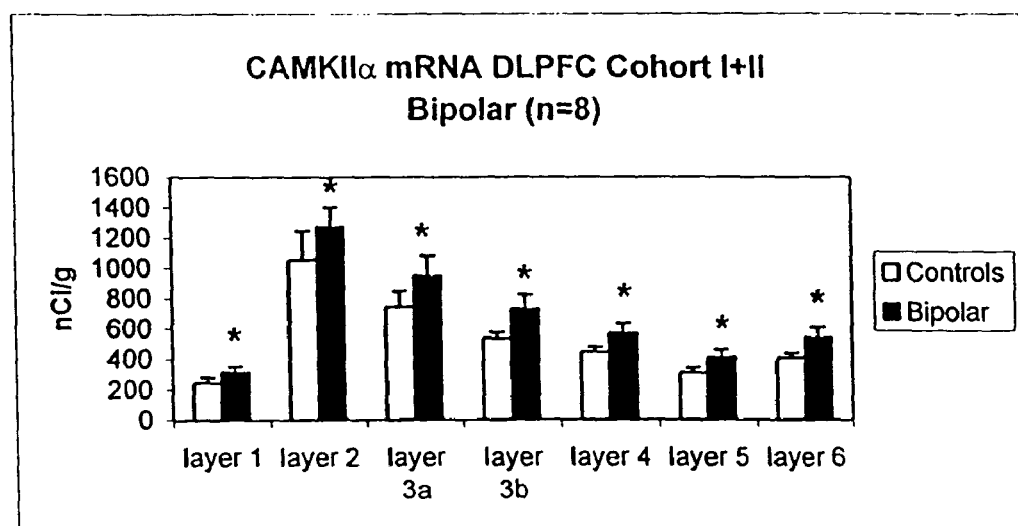
FIG. 5 shows CAMKII-α mRNA levels in 6 layers of dorsolateral prefrontal cortex (DLPFC) in the brains of patients with bipolar disorder and normal control subjects.

To help understand the genetic basis of mental disorders, studies have been conducted to investigate the expression patterns of several genes that are expressed specifically in central nervous system (see, e.g. Molnar et al., *Soc. Biol. Psychiatry* 53:39-47 (2003)). One of the genes studied is CAMKII-α, the most abundant kinase in the central nervous system. CAMKII is expressed only in glutamatergic cortical cells and is related to the glutamatergic transmitter system of the cerebral cortex. See Benson et al., *J. Neurosci.* 11(6): 1540-1564 (1991); Jones et al., *J. Neurosci.* 14:611-629 (1994). The expression of CAMKII is detected in both pyramidal and non-pyramidal glutamatergic neurons, and it is believed to play an important role in synaptic plasticity. See Kelly, *Mol. Neurobiol.* 5:153-177 (1991); Schulman and Hanson, *Neurochem. Res.* 18:65-77 (1993).

Another gene that has been studied is TBR1. Extensively expressed in the vertebrate central nervous system, TBR1 is a putative transcription factor found in post-mitotic cells of the forebrain, and is related to the Brachyury gene (or the T locus gene), which encodes a transcription factor essential for axial mesoderm development (Herrmann et al., *Nature* 343:617-622 (1990)). Several related genes have been identified for containing the sequence encoding a so-called T-box, i.e., a homologous region characteristic for this family of gene products. See e.g., U.S. Pat. Nos. 6,031,078; 6,037,148; 6,291,193 B1. Though the onset of TBR1 expression is during embryogenesis, its expression remains detectable in the adult brain, preferentially in specific layers of the cerebral cortex. See Bulfone et al., *Neuron* 15:63-78 (1995).

The present invention demonstrates the altered expression of CAMKII and TBR1 at mRNA level in the brains of patients with mental disorders (e.g., bipolar disorder and schizophrenia) in comparison with normal individuals. Furthermore, a related gene, CAMKI, also shows altered expression in the brains of patients with mental disorders. This invention thus provides methods for diagnosis of mental disorders such as mood disorders (e.g., bipolar disorder, major depression, and the like), psychosis (e.g., schizophrenia, delusions, hallucinations, and the like), and other mental disorders having a genetic component by detecting the level of a transcript or translation product of CAMKI, CAMKII or TBR1. The invention further provides methods of identifying a compound useful for the treatment of such disorders by selecting compounds that modulates the functional effect of the translation products or the expression of the transcripts described herein. The invention also provides for methods of treating patients with such mental disorders, e.g., by administering the compounds of the invention or by gene therapy.

II. General Recombinant Nucleic Acid Methods for Use with the Invention

In numerous embodiments of the present invention, polynucleotides of the invention will be isolated and cloned using recombinant methods. Such polynucleotides include, e.g., SEQ ID NOs:1 and 3, which can be used for, e.g., protein expression or during the generation of variants, derivatives, expression cassettes, or other sequences derived from SEQ ID NOs:1 and 3, to monitor gene expression, for the isolation or detection of sequences of the invention in different species, for diagnostic purposes in a patient, e.g., to detect mutations or to detect expression levels of nucleic acids or polypeptides of the invention. In some embodiments, the sequences of the invention are operably linked to a heterologous promoter. In one embodiment, the nucleic acids of the invention are from any mammal, including, in particular, e.g., a human, a mouse, a rat, a primate, etc.

A. General Recombinant Nucleic Acids Methods

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Desired Proteins In general, the nucleic acids encoding the subject proteins are cloned from DNA sequence libraries that are made to encode cDNA or genomic DNA. The particular sequences can be located by hybridizing with an oligonucleotide probe, the sequence of which can be derived from the sequences of SEQ ID NOs:1 and 3, which provide a reference for PCR primers and defines suitable regions for isolating specific probes. Alternatively, where the sequence is cloned into an expression library, the expressed recombinant protein can be detected immunologically with antisera or purified antibodies made against a polypeptide comprising an amino acid sequence of SEQ ID NO:2 or 4.

Methods for making and screening genomic and cDNA libraries are well known to those of skill in the art (see, e.g., Gubler and Hoffman *Gene* 25:263-269 (1983); Benton and Davis *Science,* 196:180-182 (1977); and Sambrook, supra). Brain cells are an example of suitable cells to isolate RNA and cDNA sequences of the invention.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue and either mechanically sheared or enzymatically digested to yield fragments of preferably about 5-100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961-3965 (1975).

An alternative method combines the use of synthetic oligonucleotide primers with polymerase extension on an mRNA or DNA template. Suitable primers can be designed from specific sequences of the invention, e.g., SEQ ID NOs:1 and 3. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding a polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying polynucleotides of the invention from mammalian tissues can be derived from the sequences provided herein, in particular SEQ ID NOs:1 and 3. For a general overview of PCR, see, Innis et al. *PCR Protocols: A Guide to Methods and Applications, Academic Press,* San Diego (1990).

Synthetic oligonucleotides can be used to construct genes. This is done using a series of overlapping oligonucleotides, usually 40-120 bp in length, representing both the sense and anti-sense strands of the gene. These DNA fragments are then annealed, ligated and cloned.

A gene encoding a polypeptide of the invention, such as one comprising an amino acid sequence of SEQ ID NO:2 or 4, can be cloned using intermediate vectors before transformation into mammalian cells for expression. These intermediate vectors are typically prokaryote vectors or shuttle vectors. The proteins can be expressed in either prokaryotes, using standard methods well known to those of skill in the art, or eukaryotes as described infra.

III. Purification of Proteins of the Invention

Either naturally occurring or recombinant polypeptides of the invention can be purified for use in functional assays. Naturally occurring polypeptides, e.g., polypeptides of SEQ ID NOs:2 and 4, can be purified, for example, from mouse or human tissue such as brain or any other source of an ortholog. Recombinant polypeptides can be purified from any suitable expression system.

The polypeptides of the invention (e.g., one comprising SEQ ID NO:2 or 4) may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant polypeptides are purified. For example, proteins having established molecular adhesion properties can be reversible fused to polypeptides of the invention. With the appropriate ligand, the polypeptides can be selectively adsorbed to a purification column and then freed from the column in a relatively pure form. The fused protein is then removed by enzymatic activity. Finally the polypeptide can be purified using immunoaffinity columns.

A. Purification of Proteins from Recombinant Bacteria

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

1. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The proteins of interest, such as polypeptides comprising an amino acid sequence of SEQ ID NO:2 or 4, can also be separated from other proteins on the basis of their size, net surface charge, hydrophobicity and affinity for ligands. In addition, antibodies raised against proteins can be conjugated to column matrices and the proteins immunopurified. All of these methods are well known in the art.

It will be apparent to one of skill that chromatographic techniques can be performed at any scale and using equipment from many different manufacturers (e.g., Pharmacia Biotech).

IV. Detection of Gene Expression

Those of skill in the art will recognize that detection of expression of polynucleotides of the invention has many uses. For example, as discussed herein, detection of the level of polypeptides or polynucleotides of the invention in a patient is useful for diagnosing mood disorders or psychosis or a predisposition for a mood disorder or psychosis. Moreover, detection of gene expression is useful to identify modulators of expression of the polypeptides or polynucleotides of the invention.

A variety of methods of specific DNA and RNA measurement using nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, *"Practice and Theory of Enzyme Immunoassays," Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) *Science*, 251: 767-777; Sheldon et al. (1993) *Clinical Chemistry* 39(4): 718-719, and Kozal et al. (1996) *Nature Medicine* 2(7): 753-759.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulavski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *Proc. Nat'l Acad. Sci. USA* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) *Fundamental Immunology* Raven Press, Ltd., NY (1993); *Coligan Current Protocols in Immunology* Wiley/Greene, N.Y. (1991); Harlow and Lane *Antibodies: A Laboratory Manual* Cold Spring Harbor Press, NY (1988); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation.

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferentially human cells from the cerebellum or the hippocampus, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

V. Immunological Detection of the Polypeptides of the Invention

In addition to the detection of polynucleotide expression using nucleic acid hybridization technology, one can also use immunoassays to detect polypeptides of the invention. Immunoassays can be used to qualitatively or quantitatively analyze polypeptides. A general overview of the applicable technology can be found in Harlow & Lane, *Antibodies: A Laboratory Manual* (1988).

A. Antibodies to Target Polypeptides or Other Immunogens

Methods for producing polyclonal and monoclonal antibodies that react specifically with a protein of interest or other immunogen are known to those of skill in the art (see, e.g., Coligan, supra; and Harlow and Lane, supra; Stites et al., supra and references cited therein; Goding, supra; and Kohler and Milstein *Nature*, 256:495-497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the sequences disclosed herein and conjugated to a carrier protein can be used as an immunogen.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their cross-reactivity against unrelated proteins or even other homologous proteins from other organisms, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

A number of proteins of the invention comprising immunogens may be used to produce antibodies specifically or selectively reactive with the proteins of interest. Recombinant protein is the preferred immunogen for the production of monoclonal or polyclonal antibodies. Naturally occurring protein, such as one comprising an amino acid sequence of SEQ ID NO:2 or 4, may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., supra.

Once target protein specific antibodies are available, the protein can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio *Enzyme Immunoassay*, CRC Press, Boca Raton, Fla. (1980); Tijssen, supra; and Harlow and Lane, supra.

Immunoassays to measure target proteins in a human sample may use a polyclonal antiserum that was raised to the protein (e.g., one has an amino acid sequence of SEQ ID NO:2 or 4) or a fragment thereof. This antiserum is selected to have low cross-reactivity against different proteins and any such cross-reactivity is removed by immunoabsorption prior to use in the immunoassay.

B. Immunological Binding Assays

In a preferred embodiment, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai *Methods in Cell Biology Volume 37: Antibodies in Cell Biology*, Academic Press, Inc. NY (1993); Stites, supra. Immunological binding assays (or immunoassays) typically utilize a "capture agent" to specifically bind to and often immobilize the analyte (in this case a polypeptide of the present invention or antigenic subsequences thereof). The capture agent is a moiety that specifically binds to the analyte. In a preferred embodiment, the capture agent is an antibody that specifically binds, for example, a polypeptide of the invention. The antibody may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111:1401-1406 (1973); and Akerstrom, et al. *J. Immunol.*, 135:2589-2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting proteins of interest from tissue samples may be either competitive or noncompetitive. Noncompetitive immunoassays are assays in which the amount of captured analyte (in this case the protein) is directly measured. In one preferred "sandwich" assay, for example, the capture agent (e.g., antibodies specific for a polypeptide comprising SEQ ID NO:2 or 4) can be bound directly to a solid substrate where it is immobilized. These immobilized antibodies then capture the polypeptide present in the test sample. The polypeptide thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of analyte (such as a polypeptide comprising SEQ ID NO:2 or 4) present in the sample is measured indirectly by measuring the amount of an added (exogenous) analyte displaced (or competed away) from a capture agent (e.g., an antibody specific for the analyte) by the analyte present in the sample. In one competitive assay, a known amount of, in this case, the protein of interest is added to the sample and the sample is then contacted with a capture agent, in this case an antibody that specifically binds to a polypeptide of the invention. The amount of immunogen bound to the antibody is inversely proportional to the concentration of immunogen present in the sample. In a particularly preferred embodiment, the antibody is immobilized on a solid substrate. For example, the amount of the polypeptide bound to the antibody may be determined either by measuring the amount of subject protein present in a protein/antibody complex or, alternatively, by measuring the amount of remaining uncomplexed protein. The amount of protein may be detected by providing a labeled protein molecule.

Immunoassays in the competitive binding format can be used for cross-reactivity determinations. For example, a protein comprising SEQ ID NO:2 or 4 can be immobilized on a solid support. Proteins are added to the assay which compete with the binding of the antisera to the immobilized antigen. The ability of the above proteins to compete with the binding of the antisera to the immobilized protein is compared to that of the protein comprising SEQ ID NO:2 or 4. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

3. Other Assay Formats

In a particularly preferred embodiment, western blot (immunoblot) analysis is used to detect and quantify the presence of a polypeptide of the invention in the sample. The technique generally comprises separating sample proteins by gel electrophoresis on the basis of molecular weight, transferring the separated proteins to a suitable solid support (such as, e.g., a nitrocellulose filter, a nylon filter, or a derivatized nylon filter) and incubating the sample with the antibodies that specifically bind the protein of interest. For example, the antibodies specifically bind to a polypeptide comprising SEQ ID NO:2 or 4 on the solid support. These antibodies may be directly labeled or alternatively may be subsequently detected using labeled antibodies (e.g., labeled sheep anti-mouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

4. Labels

The particular label or detectable group used in the assay is not a critical aspect of the invention, as long as it does not significantly interfere with the specific binding of the antibody used in the assay. The detectable group can be any material having a detectable physical or chemical property.

Such detectable labels have been well developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple calorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

VI. Screening for Modulators of Polypeptides and Polynucleotides of the Invention Modulators of polypeptides or polynucleotides of the invention, i.e. agonists or antagonists of their activity or modulators of polypeptide or polynucleotide expression, are useful for treating a number of human diseases, including mood disorders or psychosis. Administration of agonists, antagonists or other agents that modulate expression of the polynucleotides or polypeptides of the invention can be used to treat patients with mood disorders or psychosis.

A. Screening Methods

A number of different screening protocols can be utilized to identify agents that modulate the level of expression or activity of polypeptides and polynucleotides of the invention in cells, particularly mammalian cells, and especially human cells. In general terms, the screening methods involve screening a plurality of agents to identify an agent that modulates the polypeptide activity by binding to a polypeptide of the invention, modulating inhibitor binding to the polypeptide or activating expression of the polypeptide or polynucleotide, for example.

1. Binding Assays

Preliminary screens can be conducted by screening for agents capable of binding to a polypeptide of the invention, as at least some of the agents so identified are likely modulators of polypeptide activity. The binding assays usually involve contacting a polypeptide of the invention with one or more test agents and allowing sufficient time for the protein and test agents to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet and Yamamura (1985) "Neurotransmitter, Hormone or Drug Receptor Binding Methods," in *Neurotransmitter Receptor* Binding (Yamamura, H. I., et al., eds.), pp. 61-89. The protein utilized in such assays can be naturally expressed, cloned or synthesized.

Binding assays are also useful, e.g., for identifying endogenous proteins that interact with a polypeptide of the invention. For example, antibodies, receptors or other molecules that bind a polypeptide of the invention can be identified in binding assays.

2. Expression Assays

Certain screening methods involve screening for a compound that up or down-regulates the expression of a polypeptide or polynucleotide of the invention. Such methods generally involve conducting cell-based assays in which test compounds are contacted with one or more cells expressing a polypeptide or polynucleotide of the invention and then detecting an increase or decrease in expression (either transcript, translation product, or catalytic product). Some assays are performed with peripheral cells, or other cells, that express an endogenous polypeptide or polynucleotide of the invention.

Polypeptide or polynucleotide expression can be detected in a number of different ways. As described infra, the expression level of a polynucleotide of the invention in a cell can be determined by probing the mRNA expressed in a cell with a probe that specifically hybridizes with a transcript (or complementary nucleic acid derived therefrom) of a polynucleotide of the invention. Probing can be conducted by lysing the cells and conducting Northern blots or without lysing the cells using in situ-hybridization techniques. Alternatively, a polypeptide of the invention can be detected using immunological methods in which a cell lysate is probed with antibodies that specifically bind to a polypeptide of the invention.

Other cell-based assays are reporter assays conducted with cells that do not express a polypeptide or polynucleotide of the invention. Certain of these assays are conducted with a heterologous nucleic acid construct that includes a promoter of a polynucleotide of the invention that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, chloramphenicol acetyl transferase (CAT); Alton and Vapnek (1979) *Nature* 282:864-869), luciferase, β-galactosidase, green fluorescent protein (GFP) and alkaline phosphatase (Toh, et al. (1980) *Eur. J. Biochem.* 182:231-238; and Hall et al. (1983) *J. Mol. Appl. Gen.* 2:101).

In these assays, cells harboring the reporter construct are contacted with a test compound. A test compound that either activates the promoter by binding to it or triggers a cascade that produces a molecule that activates the promoter causes expression of the detectable reporter. Certain other reporter assays are conducted with cells that harbor a heterologous construct that includes a transcriptional control element that activates expression of a polynucleotide of the invention and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

The level of expression or activity can be compared to a baseline value. As indicated above, the baseline value can be a value for a control sample or a statistical value that is representative of expression levels for a control population (e.g., healthy individuals not having or at risk for mood disorders or psychosis). Expression levels can also be determined for cells that do not express a polynucleotide of the invention as a negative control. Such cells generally are otherwise substantially genetically the same as the test cells.

A variety of different types of cells can be utilized in the reporter assays. Cells that express an endogenous polypeptide or polynucleotide of the invention include, e.g., brain cells, including cells from the cerebellum, cingulate cortex, or dorsolateral prefrontal cortex. Cells that do not endogenously express polynucleotides of the invention can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

3. Catalytic Activity

Catalytic activity of polypeptides of the invention can be determined by measuring the production of enzymatic products or by measuring the consumption of substrates. Activity refers to either the rate of catalysis or the ability to the polypeptide to bind ($K_m$) the substrate or release the catalytic product ($K_d$).

Analysis of the activity of polypeptides of the invention are performed according to general biochemical analyses. Such assays include cell-based assays as well as in vitro assays involving purified or partially purified polypeptides or crude cell lysates. The assays generally involve providing a known quantity of substrate and quantifying product as a function of time.

For example, without intending to limit the present invention, SEQ ID NO:1 encodes CAMKII-α, a kinase. Therefore, modulators of CAMKII-α can be identified by detecting alterations in CAMKII-α activity in cells or in vitro upon contact with the modulator.

4. Validation

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if expression or activity of a polynucleotide or polypeptide of the invention is in fact upregulated. The animal models utilized in validation studies generally are mammals of any kind. Specific examples of suitable animals include, but are not limited to, primates, mice, and rats.

5. Animal Models

Animal models of mental disorders also find use in screening for modulators. In one embodiment, invertebrate models such as *Drosophila* models can be used, screening for modulators of *Drosophila* orthologs of the human genes disclosed herein. In another embodiment, transgenic animal technology including gene knockout technology, for example as a result of homologous recombination with an appropriate gene targeting vector, or gene overexpression, will result in the absence, decreased or increased expression of a polynucleotide or polypeptide of the invention. The same technology can also be applied to make knockout cells. When desired, tissue-specific expression or knockout of a polynucleotide or polypeptide of the invention may be necessary. Transgenic animals generated by such methods find use as animal models of mental illness and are useful in screening for modulators of mental illness.

Knockout cells and transgenic mice can be made by insertion of a marker gene or other heterologous gene into an endogenous gene site (e.g., the CAMKII-α gene or the TBR1 gene) in the mouse genome via homologous recombination. Such mice can also be made by substituting an endogenous polynucleotide of the invention with a mutated version of the polynucleotide, or by mutating an endogenous polynucleotide, e.g., by exposure to carcinogens.

For development of appropriate stem cells, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators of Polypeptides or Polynucleotides of the Invention

The agents tested as modulators of the polypeptides or polynucleotides of the invention can be any small chemical compound, or a biological entity, such as a protein, sugar, nucleic acid or lipid. Alternatively, modulators can be genetically altered versions of a polypeptide or polynucleotide of the invention. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like. Modulators also include agents designed to reduce the level of mRNA of the invention (e.g. antisense molecules, ribozymes, DNAzymes and the like) or the level of translation from an mRNA.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md., etc.).

C. Solid State and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule that binds the tag (a tag binder) is fixed to a solid support, and the tagged molecule of interest (e.g., a polynucleotide of SEQ ID NO:1 or 3, or a polypeptide of SEQ ID NO:2 or 4) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:7). Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank and Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the expression or activity of the polynucleotides or polypeptides of the invention. In a preferred embodiment, the methods of the invention include such a control reaction. For each of the assay formats described, "no modulator" control reactions that do not include a modulator provide a background level of binding activity.

In some assays it will be desirable to have positive controls to ensure that the components of the assays are working properly. At least two types of positive controls are appropriate. First, a known activator of a polynucleotide or polypeptide of the invention can be incubated with one sample of the assay, and the resulting increase in signal resulting from an increased expression level or activity of polynucleotide or polypeptide determined according to the methods herein. Second, a known inhibitor of a polynucleotide or polypeptide of the invention can be added, and the resulting decrease in signal for the expression or activity can be similarly detected.

D. Computer-Based Assays

Yet another assay for compounds that modulate the activity of a polypeptide or polynucleotide of the invention involves computer assisted drug design, in which a computer system is used to generate a three-dimensional structure of the polypeptide or polynucleotide based on the structural information encoded by its amino acid or nucleotide sequence. The input sequence interacts directly and actively with a pre-established algorithm in a computer program to yield secondary, tertiary, and quaternary structural models of the molecule. Similar analyses can be performed on potential receptors or binding partners of the polypeptides or polynucleotides of the invention. The models of the protein or nucleotide structure are then examined to identify regions of the structure that have the ability to bind, e.g., a polypeptide or polynucleotide of the invention. These regions are then used to identify polypeptides that bind to a polypeptide or polynucleotide of the invention.

The three-dimensional structural model of a protein is generated by entering protein amino acid sequences of at least 10 amino acid residues or corresponding nucleic acid sequences encoding a potential receptor into the computer system. The amino acid sequences encoded by the nucleic acid sequences provided herein represent the primary sequences or subsequences of the proteins, which encode the structural information of the proteins. At least 10 residues of an amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary, and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of a polypeptide or polynucleotide of the invention to identify binding sites of the polypeptide or polynucleotide of the invention. Binding affinity between the protein and ligands is determined using energy terms to determine which ligands have an enhanced probability of binding to the protein.

Computer systems are also used to screen for mutations, polymorphic variants, alleles and interspecies homologs of genes encoding a polypeptide or polynucleotide of the invention. Such mutations can be associated with disease states or genetic traits. As described above, GeneChip™ and related technology can also be used to screen for mutations, polymorphic variants, alleles and interspecies homologs. Once the variants are identified, diagnostic assays can be used to identify patients having such mutated genes. Identification of the mutated a polypeptide or polynucleotide of the invention involves receiving input of a first amino acid sequence of a polypeptide of the invention (or of a first nucleic acid sequence encoding a polypeptide of the invention), e.g., any amino acid sequence having at least 60%, optionally at least 70% or 85%, identity with the amino acid sequence encoded by SEQ ID NOs:1 and 3, or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various polynucleotides of the invention, and mutations associated with disease states and genetic traits.

VII. Compositions, Kits and Integrated Systems

The invention provides compositions, kits and integrated systems for practicing the assays described herein using polypeptides or polynucleotides of the invention, antibodies specific for polypeptides or polynucleotides of the invention, etc.

The invention provides assay compositions for use in solid phase assays; such compositions can include, for example, one or more polynucleotides or polypeptides of the invention (such as a polynucleotide comprising SEQ ID NO:1 or 3, or a polypeptide comprising SEQ ID NO:2 or 4) immobilized on a solid support, and a labeling reagent. In each case, the assay compositions can also include additional reagents that are desirable for hybridization. Modulators of expression or activity of polynucleotides or polypeptides of the invention can also be included in the assay compositions.

The invention also provides kits for carrying out the assays of the invention. The kits typically include a probe that comprises an antibody that specifically binds to polypeptides or polynucleotides of the invention, and a label for detecting the presence of the probe. The kits may include several polynucleotide sequences encoding polypeptides of the invention. Kits can include any of the compositions noted above, and optionally further include additional components such as instructions to practice a high-throughput method of assaying for an effect on expression of the genes encoding the polypeptides of the invention, or on activity of the polypeptides of the invention, one or more containers or compartments (e.g., to hold the probe, labels, or the like), a control modulator of the expression or activity of polypeptides of the invention, a robotic armature for mixing kit components or the like.

The invention also provides integrated systems for high-throughput screening of potential modulators for an effect on the expression or activity of the polypeptides of the invention. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous STAT binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS®, OS2® WINDOWS®, WINDOWS NT®, WINDOWS95®, WINDOWS98®, or WINDOWS2000® based computers), MACINTOSH®, or UNIX® based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

VIII. Administration and Pharmaceutical Compositions

Modulators of the polynucleotides or polypeptides of the invention (e.g., antagonists or agonists) can be administered directly to a mammalian subject for modulation of activity of those molecules in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

Diseases that can be treated include the following, which include the corresponding reference number from Morrison, *DSM-IV Made Easy*, 1995: Schizophrenia, Catatonic, Subchronic, (295.21); Schizophrenia, Catatonic, Chronic (295.22); Schizophrenia, Catatonic, Subchronic with Acute Exacerbation (295.23); Schizophrenia, Catatonic, Chronic with Acute Exacerbation (295.24); Schizophrenia, Catatonic, in Remission (295.55); Schizophrenia, Catatonic, Unspecified (295.20); Schizophrenia, Disorganized, Subchronic (295.11); Schizophrenia, Disorganized, Chronic (295.12); Schizophrenia, Disorganized, Subchronic with Acute Exacerbation (295.13); Schizophrenia, Disorganized, Chronic with Acute Exacerbation (295.14); Schizophrenia, Disorganized, in Remission (295.15); Schizophrenia, Disorganized, Unspecified (295.10); Schizophrenia, Paranoid, Subchronic (295.31); Schizophrenia, Paranoid, Chronic (295.32); Schizophrenia, Paranoid, Subchronic with Acute Exacerbation (295.33); Schizophrenia, Paranoid, Chronic with Acute Exacerbation (295.34); Schizophrenia, Paranoid, in Remission (295.35); Schizophrenia, Paranoid, Unspecified (295.30); Schizophrenia, Undifferentiated, Subchronic (295.91); Schizophrenia, Undifferentiated, Chronic (295.92); Schizophrenia, Undifferentiated, Subchronic with Acute Exacerbation (295.93); Schizophrenia, Undifferentiated, Chronic with Acute Exacerbation (295.94); Schizophrenia, Undifferentiated, in Remission (295.95); Schizophrenia, Undifferentiated, Unspecified (295.90); Schizophrenia, Residual, Subchronic (295.61); Schizophrenia, Residual, Chronic (295.62); Schizophrenia, Residual, Subchronic with Acute Exacerbation (295.63); Schizophrenia, Residual, Chronic with Acute Exacerbation (295.94); Schizophrenia, Residual, in Remission (295.65); Schizophrenia, Residual, Unspecified (295.60); Delusional (Paranoid) Disorder (297.10); Brief Reactive Psychosis (298.80); Schizophreniform Disorder (295.40); Schizoaffective Disorder (295.70); Induced Psychotic Disorder (297.30); Psychotic Disorder NOS (Atypical Psychosis) (298.90); Personality Disorders, Paranoid (301.00); Personality Disorders, Schizoid (301.20); Personality Disorders, Schizotypal (301.22); Personality Disorders, Antisocial (301.70); Personality Disorders, Borderline (301.83) and bipolar disorders, maniac, hypomaniac, dysthymic or cyclothymic disorders, substance-induced mood disorders, major depression, psychosis, including paranoid psychosis, catatonic psychosis, delusional psychosis, having schizoaffective disorder, and substance-induced psychotic disorder.

In some embodiments, modulators of polynucleotides or polypeptides of the invention can be combined with other drugs useful for treating mental disorders including useful for treating mood disorders, e.g., schizophrenia, bipolar disorders, or major depression. In some preferred embodiments, pharmaceutical compositions of the invention comprise a modulator of a polypeptide of polynucleotide of the invention combined with at least one of the compounds useful for treating schizophrenia, bipolar disorder, or major depression, e.g., such as those described in U.S. Pat. Nos. 6,297,262; 6,284,760; 6,284,771; 6,232,326; 6,187,752; 6,117,890; 6,239,162 or 6,166,008.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17th ed. 1985)).

The modulators (e.g., agonists or antagonists) of the expression or activity of the a polypeptide or polynucleotide of the invention, alone or in combination with other suitable components, can be made into aerosol formulations (i.e., they can be "nebulized") to be administered via inhalation or in compositions useful for injection. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to effect a beneficial response in the subject over time. The optimal dose level for any patient will depend on a variety of factors including the efficacy of the specific modulator employed, the age, body weight, physical activity, and diet of the patient, on a possible combination with other drugs, and on the severity of the mental disorder. The size of the dose also will be determined by the existence, nature, and extent of any adverse side effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side effects of the modulator at various concentrations, as applied to the mass and overall health of the subject. Administration can be accomplished via single or divided doses.

IX. Gene Therapy Applications

A variety of human diseases can be treated by therapeutic approaches that involve stably introducing a gene into a human cell such that the gene is transcribed and the gene product is produced in the cell. Diseases amenable to treatment by this approach include inherited diseases, including those in which the defect is in a single or multiple genes. Gene therapy is also useful for treatment of acquired diseases and other conditions. For discussions on the application of gene therapy towards the treatment of genetic as well as acquired diseases, see, Miller, *Nature* 357:455-460 (1992); and Mulligan, *Science* 260:926-932 (1993).

In the context of the present invention, gene therapy can be used for treating a variety of disorders and/or diseases in which the polynucleotides and polypeptides of the invention has been implicated. For example, compounds, including polynucleotides, can be identified by the methods of the present invention as effective in treating a mental disorder. Introduction by gene therapy of these polynucleotides can then be used to treat, e.g., mental disorders including mood disorders psychosis.

A. Vectors for Gene Delivery

For delivery to a cell or organism, the polynucleotides of the invention can be incorporated into a vector. Examples of vectors used for such purposes include expression plasmids capable of directing the expression of the nucleic acids in the target cell. In other instances, the vector is a viral vector system wherein the nucleic acids are incorporated into a viral genome that is capable of transfecting the target cell. In a preferred embodiment, the polynucleotides can be operably linked to expression and control sequences that can direct expression of the gene in the desired target host cells. Thus, one can achieve expression of the nucleic acid under appropriate conditions in the target cell.

B. Gene Delivery Systems

Viral vector systems useful in the expression of the nucleic acids include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the genes of interest are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors are also useful for introducing the nucleic acids of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.*, 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis-acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA*, 81:6349-6353 (1984); Danos and Mulligan *Proceedings of the National Academy of Sciences, USA*, 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

In some embodiments of the invention, an antisense polynucleotide is administered which hybridizes to a gene encoding a polypeptide of the invention (such as CAMKII-α or TBR1). The antisense polypeptide can be provided as an antisense oligonucleotide (see, e.g., Murayama et al., *Antisense Nucleic Acid Drug Dev.* 7:109-114 (1997)). Genes encoding an antisense nucleic acid can also be provided; such genes can be introduced into cells by methods known to those of skill in the art. For example, one can introduce an antisense nucleotide sequence in a viral vector, such as, for example, in hepatitis B virus (see, e.g., Ji et al., *J. Viral*

Hepat. 4:167-173 (1997)), in adeno-associated virus (see, e.g., Xiao et al., *Brain Res.* 756:76-83 (1997)), or in other systems including, but not limited, to an HVJ (Sendai virus)-liposome gene delivery system (see, e.g., Kaneda et al., *Ann. NY Acad. Sci.* 811:299-308 (1997)), a "peptide vector" (see, e.g., Vidal et al., *CR Acad. Sci III* 32:279-287 (1997)), as a gene in an episomal or plasmid vector (see, e.g., Cooper et al., *Proc. Natl. Acad. Sci. U.S.A.* 94:6450-6455 (1997), Yew et al. *Hum Gene Ther.* 8:575-584 (1997)), as a gene in a peptide-DNA aggregate (see, e.g., Niidome et al., *J. Biol. Chem.* 272:15307-15312 (1997)), as "naked DNA" (see, e.g., U.S. Pat. Nos. 5,580,859 and 5,589,466), in lipidic vector systems (see, e.g., Lee et al., *Crit Rev Ther Drug Carrier Syst.* 14:173-206 (1997)), polymer coated liposomes (U.S. Pat. Nos. 5,213,804 and 5,013,556), cationic liposomes (Epand et al., U.S. Pat. Nos. 5,283,185; 5,578,475; 5,279,833; and 5,334,761), gas filled microspheres (U.S. Pat. No. 5,542,935), ligand-targeted encapsulated macromolecules (U.S. Pat. Nos. 5,108,921; 5,521,291; 5,554,386; and 5,166,320).

C. Pharmaceutical Formulations

When used for pharmaceutical purposes, the vectors used for gene therapy are formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer, or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans; antioxidants, such as ascorbic acid or glutathione; chelating agents; low molecular weight proteins or other stabilizers or excipients. Other physiologically acceptable compounds include wetting agents, emulsifying agents, dispersing agents, or preservatives, which are particularly useful for preventing the growth or action of microorganisms. Various preservatives are well known and include, for example, phenol and ascorbic acid. Examples of carriers, stabilizers, or adjuvants can be found in Remington's *Pharmaceutical Sciences*, Mack Publishing Company, Philadelphia, Pa., 17th ed. (1985).

D. Administration of Formulations

The formulations of the invention can be delivered to any tissue or organ using any delivery method known to the ordinarily skilled artisan. In some embodiments of the invention, the nucleic acids of the invention are formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701.

E. Methods of Treatment

The gene therapy formulations of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, or biolistics. In further embodiments, the nucleic acids are taken up directly by the tissue of interest.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6):2414-9 (1996); Koc et al., *Seminars in Oncology* 23 (1):46-65 (1996); Raper et al., *Annals of Surgery* 223(2): 116-26 (1996); Dalesandro et al., *J. Thorac. Cardi. Surg.*, 11(2):416-22 (1996); and Makarov et al., *Proc. Natl. Acad. Sci. USA* 93(1):402-6 (1996).

X. Diagnosis of Mood Disorders and Psychosis

The present invention also provides methods of diagnosing mood disorders (such as major depression or bipolar disorder), psychosis (such as schizophrenia), or a predisposition of at least some of the pathologies of such disorders. Diagnosis involves determining the level of a polypeptide or polynucleotide of the invention in a patient and then comparing the level to a baseline or range. Typically, the baseline value is representative of a polypeptide or polynucleotide of the invention in a healthy person not suffering from a mood disorder or psychosis or under the effects of medication or other drugs. Variation of levels of a polypeptide or polynucleotide of the invention from the baseline range indicates that the patient has a mood disorder or psychosis or at risk of developing at least some aspects of a mood disorder or psychosis. In some embodiments, the level of a polypeptide or polynucleotide of the invention are measured by taking a blood, urine or tissue sample from a patient and measuring the amount of a polypeptide or polynucleotide of the invention in the sample using any number of detection methods, such as those discussed herein.

In some embodiments, the level of the enzymatic product of a polypeptide or polynucleotide of the invention (such as the catalytic activity of CAMKII-$\alpha$) is measured and compared to a baseline value of a healthy person or persons. Modulated levels of the product compared to the baseline indicates that the patient has a mood disorder or psychosis or is at risk of developing at least some aspects of a mood disorder or psychosis. Patient samples, for example, can be blood, urine or tissue samples.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

TBR1 and CAMKII-$\alpha$ Expression in Bipolar Patients

This example compared the mRNA levels of CAMKII-$\alpha$ and TBR1 in various layers of the cerebral cortex in the brains of patients suffering from bipolar disorder with those found in non-psychiatric control subjects. In situ hybridization histochemistry demonstrated significantly increased level of CAMKII-$\alpha$ mRNA in all 6 layers and significantly increased level of TBR1 mRNA in layers III, IV, V, and VI of dorsolateral prefrontal cortex (DLPFC) in the brains of bipolar patients. In addition, the beta isoform of subunit of CAMK II is upregulated in the anterior cingulate and the DLPFC of patients diagnosed with major depression and in the anterior cingulated in patients diagnosed with bipolar disease. Furthermore, CAMKI showed upregulation in the anterior cingulate in patients with mood disorders.

Methods

A. Acquisition, Storage, and Fixation of Brain Tissue

Brain samples from the dorsolateral prefrontal cortex (area 9) of the left hemisphere were taken from 8 patients suffering from bipolar disorder and from 8 non-psychiatric control subjects. Brain tissue was obtained from Brain Bank (The University of California, Irvine) and Brain Tissue Repository of the Center for Neuroscience (The University of California, Davis). The diagnoses of the patients were made by Board-certified psychiatrists using the DSM-IV criteria (*American Diagnostic and Statistical Manual*, 4th Ed. 1994). Brains of the non-psychiatric control subjects were matched to patients with bipolar disorder by age, sex, and autolysis time (Table 1). Control subjects had no clinical history of neurological or psychiatric disease or of substance abuse. Patients with bipolar disorders did not suffer from chronic alcoholism of other potentially relevant conditions. After autopsy, brains were cooled to 4° C., cut into coronal slices slightly less than 1 cm thick, flash-frozen between two supercooled aluminum plates, and stored at −85° C., as described by Jones et al. (*J. Neurosci. Methods* 44: 133-144 (1992).)

For in situ hybridization histochemistry, small blocks were cut from the left dorsolateral prefrontal cortex (DLPFC) from each brain. Blocks were raised to approximately 4° C., placed in cold 4% paraformaldehyde in 0.1 M phosphate buffer (pH 7.4) overnight, infiltrated with 30% sucrose in 0.1 M phosphate buffer, refrozen in dry ice, and kept at −85° C. until sectioning.

TABLE 1

| Pair | Gender | Age | PMI | COD |
|---|---|---|---|---|
| Bipolar 1 | Female | 56 | 29 | Suicide |
| Bipolar 2 | Male | 22 | 9 | Suicide |
| Bipolar 3 | Male | 52 | 28 | Suicide |
| Bipolar 4 | Male | 69 | 11.3 | Suicide |
| Bipolar 5 | Female | 63 | 22 | Cardiac |
| Bipolar 6 | Female | 68 | 25.5 | Aspirated |
| Bipolar 7 | Male | 59 | 15.5 | Cardiac |
| Bipolar 8 | Male | 69 | 28.5 | Natural |
| Control 1 | Female | 60 | 24 | Cardiac |
| Control 2 | Male | 19 | 6.5 | Trauma |
| Control 3 | Male | 54 | 25 | Cardiac |
| Control 4 | Male | 72 | 15 | Cancer |
| Control 5 | Female | 64 | 27 | Colon Cancer |
| Control 6 | Female | 68 | 25 | Ovarian Cancer |
| Control 7 | Male | 58 | 15.3 | Abdominal Cancer |
| Control 8 | Male | 70 | 27 | ASHD |

B. In Situ Hybridization Procedure and Quantitative Analysis

For in situ hybridization experiments, serial sections 50 μm thick were cut on a sliding microtome and collected in groups of 6. One group was processed for standard Nissl staining. The remaining sections were stored in 4% paraformaldehyde in 0.1 M phosphate buffer for at least 7 days and processed for in situ hybridization histochemistry.

Free-floating sections were hybridized with [α-$^{33}$P]UTP-labeled antisense (or sense) riboprobes transcribed from linearized cDNA templates. CAMKII-α riboprobes were transcribed from 350 nucleotide monkey cDNA, as described by Benson et al., *J. Neurosci.* 11(1):31-47, (1991). TBR1 riboprobes were transcribed from a 1.2 kb human TBR1 cDNA, as described by Bulfone et al, *Neuron* 15:63-78, (1995).

Free-floating sections were prepared for in situ hybridization by washing in 0.1 M glycine in 0.1 M phosphate buffer (pH 7.4) followed by two washes in 0.1 M phosphate buffer (pH 7.4) and 2 washes in 2× saline sodium citrate (SSC; sodium chloride/sodium citrate solution, pH 7.0). Sections were then incubated in hybridization solution containing 50% formamide, 10% dextran sulfate, 0.7% Ficoll, 0.7% polyvinyl pyrolidone, 0.5 mg/ml yeast tRNA, 0.33 mg/ml denatured herring sperm DNA, 20 mM dithiothreitol (DTT), and $5.0 \times 10^5$ cpm/ml of the $^{33}$P-radiolabeled antisense or sense probe. Hybridization was carried out overnight at 60° C. in a humid chamber.

After hybridization, sections were washed twice in 4×SSC at 60° C., digested with 20 μg/ml of ribonuclease A (pH 8.0) for 30 minutes at 45° C., and washed through descending concentrations of SSC to a final stringency of 0.5×SSC. Sections were mounted on gelatin-coated slides, dried, and exposed to Amersham β-max film for 4-15 days. After development of the film, sections were lipid-extracted in chloroform, dipped in Kodak NTB2 emulsion (diluted 1:1 with water), exposed for 8 days at 4° C., developed in Kodak D-19, fixed, and counterstained with thionin.

Film autoradiograms of hybridized sections were quantified by taking optical density measurements using a microcomputer imaging device (MCID/M5; Imaging Research, St. Catharine's Ontario, Canada). Mean gray-levels recorded by the system in each sample and reported as integrated optical density (IOD) value were converted to units of radioactivity (nCi/g) based on a set of $^{14}$C radioactive standards (Amersham) exposed on each film. At least six samples within each cortical layer were taken in at least three sections for each brain. The level of the background labeling as measured over the white matter was subtracted from each individual measurement in all layer, in each brain.

C. Statistical Analysis

For each brain and cortical layer, the mean values of CAMKII-α and TBR1 mRNA were calculated, and then the mean value and SEM for each of the two cohorts were calculated from the 8 singles means. Statistical significance between the mean values of depressed and controls was determined by using SAS software and repeated measures analysis of variance (RMANOVA), using two cohorts as groups and cortical layers as variates. In addition, Students' two-tailed paired t-test was used to determine significance of differences between the six cohorts for each cortical layer separately.

Results

In general each probe showed labeling of all 6 layers with a laminar pattern specific for each mRNA. Sense controls revealed only nonspecific background labeling.

CAMKII-α labeling pattern was typically diffuse, reflecting the presence of high densities of the mRNA in dendrites as well as in somata. See Burgin et al., *J. Neurosci.* 10:1788-1798. (1990); Benson et al., *J. Neurosci.* 11(6):1540-1564. (1990). Dense hybridization occurred in layers II and IIIa. Labeling in layers IV and V was lighter but clearly above background. The degree of hybridization is significantly higher in all six layers of patients suffering from bipolar disorder compared to control subjects, indicating increased CAMKII-α expression at mRNA level (FIG. 5).

Figure 6:
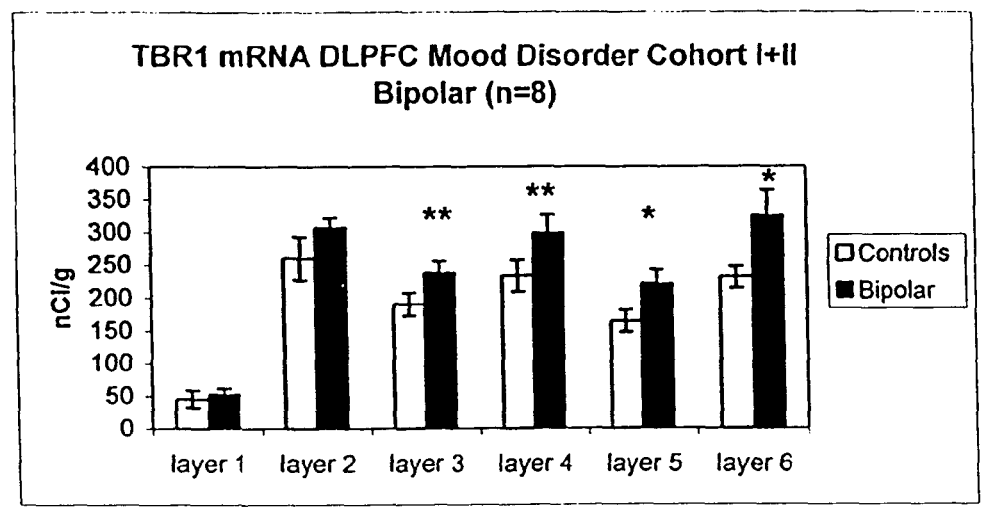
FIG. 6 shows TBR1 mRNA levels in 6 layers of dorsolateral prefrontal cortex (DLPFC) in the brains of patients with bipolar disorder and normal control subjects.

Labeling for TBR1 mRNA was diffuse and present in all layers, with the highest level in layer VI. The mRNA levels in all 6 layers appeared higher in the brains of bipolar patients (FIG. 6). Statistical analysis showed that the mean density of TBR1 mRNA in bipolar patients was increased in layers III, IV, V, and VI (ANOVA F=15.99, P<0.001). Two-tailed paired t-test analysis on individual layers showed a statistically significant increase in layers III, IV, V, and VI, where the increase was 25%, 34%, 34%, and 48%, respectively.

Discussion

As this example shows increased mRNA levels of CAMKII-α and TBR1 in the brain of bipolar disorder patients, the neurobiological implications of such differential expression are significant since these genes are expressed in the central nervous system in a tissue-specific manner and their altered expression levels are likely involved in the development of a variety of neuropsychiatric disorders. Thus, the mRNA levels of CAMKII-α and TBR1 can be used as indicators to diagnose patients with certain neuropsychiatric disorders, or to detect those with increased likelihood of developing such disorders. Relying on these indicators, compounds for treatment of such mental disorders can be quickly identified, methods of treatment can be properly developed and evaluated, and individuals with these disorders may be effectively treated or even cured.

Example II

Expression of TBR1 in Schizophrenic Patients

Dysfunction of the prefrontal cortex is believed to be a central feature underlying the cognitive abnormalities observed in schizophrenic patients. This dysfunction may be related to alterations in glutamatergic or gamma aminobutyric acid neurotransmission based on defective cortical connectivity. T-brain-1(TBR1) is a transcription factor mainly expressed in glutamatergic cortical neurons during early development. Studies in rodents show that disruption of TBR1 expression leads to profound alterations of corticocortical and cortico-thalamic connectivity. In the present study we investigated the expression of TBR1 mRNA in the dorsolateral prefrontal cortex of schizophrenic patients compared to matched controls. We found a trend toward reduced expression of TBR1 mRNA in all layers, and a statistically significant reduction in layer III whose cells are the main sources of cortico-cortical connections. Our data suggest an involvement of this transcription factor in the pathophysiology of schizophrenia, and that the glutamatergic neurons of the prefrontal cortex are potentially affected with consequences for cortical integration.

Introduction

Schizophrenia is a severe psychiatric disorder characterized by hallucinations, delusions, disorganized thought, and some cognitive impairments. It is widely thought that the underlying basis of schizophrenia may be in brain circuitry that is compromised during development but does not cause clinically manifest schizophrenia until subjected to life stresses during final maturation in young adulthood (Jones, 1997; Harrison 1999, Lewis and Levitt, 2002).

A considerable amount of evidence supports the idea that the severe cognitive dysfunction of schizophrenia is associated with anatomical and functional abnormalities of the dorsolateral prefrontal cortex (DLPFC). Brain imaging studies consistently demonstrate hypoactivity in this region (Andreasen et al., 1992; Buchsbaum et al., 1992; Weinberger and Berman, 1996; Hazlett et al., 2000) and suggest that the functional integrity of cortical neurons and/or their connections may be altered (Pearlson and Marsh, 1999). At a molecular level, hypoactivity in the DLPFC is likely a reflection of abnormalities in gene expression for neurotransmitter and receptor related mRNAs, suggesting a strong involvement of both γ-aminobutyric-acid (GABA)-ergic and glutamatergic neurons in the pathophysiology of the disease. The expression of GABA-ergic markers is decreased without a concomitant loss of neurons, and a selective alteration in gene expression for GABA-ergic and glutamatergic receptor subunits, have been described in the dorsolateral prefrontal cortex of schizophrenic patients (Akbarian et al., 1995; Akbarian et al., 1996a; Huntsman et al., 1998; Lewis et al., 1999).

Anatomical studies provide further evidence for a cellular pathology in the DLPFC. A particular population of cortical neurons located in the white matter was found displaced in the prefrontal and lateral temporal cortex of schizophrenic patients, suggesting a possible disturbance of neuronal development (Akbarian et al., 1996b). Cortical thickness was found reduced with a decrease in the amount of neuropil and neuronal soma size but not of neuronal cell number (Selemon and Goldman-Rakic, 1999) and decreases in synaptic and connectivity associated proteins were also found (Thompson et al., 1998; Honer et al., 1999; Karson et al., 1999; Glantz and Lewis, 2000; Weickert et al., 2001), suggesting that reduced neuronal connections may underlie functional abnormalities in the DLPFC of patients with schizophrenia.

The formation and maintenance of neuronal connections are complex processes involving the regulation of many genes and proteins. One such protein, T-brain-1 (TBR1), is a neuron specific transcription factor which is highly expressed in cortical neurons during development and is maintained into adulthood (Bulfone et al., 1995; Hevner et al., 2001). In rodents, TBR1 is mainly expressed in glutamatergic cortical neurons (Hevner et al., 2001) which are the sources of all extrinsic connections of the cortex. Analysis of mutant mice null for TBR1 indicates an important role of this transcription factor in the migration of cortical neurons and in the formation of correct corticocortical and cortico-thalamic connections during development (Hevner et al., 2001; Dwyer and O'Leary, 2001).

Because TBR1 is expressed in glutamatergic neurons which are possibly involved in the pathophysiology of schizophrenia, and because it has a role in cortical development which might be compromised in this disease, we decided to investigate the expression of TBR1 in the DLPFC of schizophrenic patients using in situ hybridization histochemistry.

Material and Methods

A. Acquisition, Storage, and Fixation of Brain Tissue

Brain samples from the dorsolateral prefrontal cortex (area 9) of the right hemisphere of 8 schizophrenic patients and 8 non-psychiatric control subjects were used in the present study. Brain tissue was obtained from the University of California, Irvine, Brain Bank and Brain Tissue Repository of the Center for Neuroscience, University of California, Davis. The diagnoses were performed by Board-certified psychiatrists using DSM-IV criteria (American Diagnostic and Statistical Manual, 4th Ed. 1994). Brains of control subjects were matched to those of the schizophrenic patients by age, sex, and autolysis time. Control subjects had no clinical history of neurological or psychiatric disease or of substance abuse. None of the patients were chronic alcoholics or suffered from other potentially relevant conditions. After autopsy, brains were cooled to 4° C., cut into coronal slices slightly less than 1 cm thick, flash-frozen between two supercooled aluminum plates, and stored at −85° C., as previously described (Jones et al., 1992).

For in situ hybridization histochemistry, small blocks were cut from the right dorsolateral prefrontal cortex from each brain. Blocks were raised to approximately 4° C., and placed in cold 4% paraformaldehyde in 0.1 M phosphate buffer (pH 7.4) overnight, infiltrated with 30% sucrose in 0.1 M phosphate buffer, refrozen in dry ice, and kept at −85° C. until sectioning.

B. In Situ Hybridization and Quantitative Analysis

For in situ hybridization histochemistry, serial sections 50 μm thick were cut on a sliding microtome and collected in 4% paraformaldehyde in 0.1 M phosphate buffer in which they remained for at least 7 days prior to processing for in situ hybridization histochemistry. Free-floating sections were hybridized with [α-$^{33}$P]UTP-labeled antisense (or sense) riboprobes transcribed from linearized cDNA templates. TBR1 riboprobes where transcribed from a 1.2 kb human TBR 1 cDNA.

Free-floating sections were prepared for in situ hybridization by washing in 0.1 M glycine in 0.1 M phosphate buffer (pH 7.4) followed by two washes in 0.1 M phosphate buffer (pH 7.4) and 2 washes in 2× saline sodium citrate (SSC; 2×SSC is 0.3 M sodium chloride and 0.03 M sodium citrate, pH 7.0). Sections were then incubated in the hybridization solution containing 50% formamide, 10%dextran sulfate, 0.7% Ficoll, 0.7% polyvinyl pyrolidone, 0.5 mg/ml yeast tRNA, 0.33 mg/ml yeast tRNA, 0.33 mg/ml denatured herring sperm DNA, 20 mM dithiothreitol (DTT), and 5.0×105 cpm/ml of the $^{33}$P-radiolabeled antisense or sense probe. Hybridization was carried overnight at 60° C. in a humid chamber.

After hybridization, sections were washed twice in 4×SSC at 60° C., digested with 20 μg/ml of ribonuclease A (pH 8.0) for 30 min at 45° C., and washed through descending concentrations of SSC to a final stringency of 0.5×SSC. Sections were mounted on gelatin-coated slides, dried, and exposed for 15 days. After development of the film, sections were lipid-extracted in chloroform, dipped in Kodak NTB2 emulsion (diluted 1:1 with water), exposed for 8 days at 4° C., developed in Kodak D-19, fixed, and counterstained with thionin.

Film autoradiograms of hybridized sections were quantified by taking optical density measurements using a microcomputer imaging device (MCID/M5; Imaging Research, St. Catharine's Ontario, Canada). Mean gray-levels recorded by the system in each sample and reported as integrated optical density (IOD) value were converted to units of radioactivity (nCi/g) based on a set of 14C radioactive standards (Amersham) exposed on each film. At least 6 samples within each cortical layer were taken in at least three sections from each brain. The level of background labeling, as measured over the white matter, was subtracted from each individual measurement in all layers, in each brain C. Statistical Analysis For each brain and cortical layer, the mean values for TBR1 mRNA levels were calculated, and the mean value and standard error for each of the two cohorts was calculated from the 16 single means. Statistical significance of differences between the mean values of schizophrenic and controls was determined by using repeated measures analysis of variance (RMANOVA), using the two cohorts as groups and cortical layers as variates. In addition, Student's two-tailed paired t-test was used to determine significance of differences between the 2 cohorts for each cortical layer separately.

Results

Sense controls of TBR1 mRNA in the dorsolateral prefrontal cortex revealed only nonspecific background labeling. TBR1 mRNA was expressed in all 6 layers of adult human DLPFC in a specific laminar pattern. Hybridization signal was higher in layers VI and IV, intermediate in layers II and III and low in layer V and I.

Figure 7:
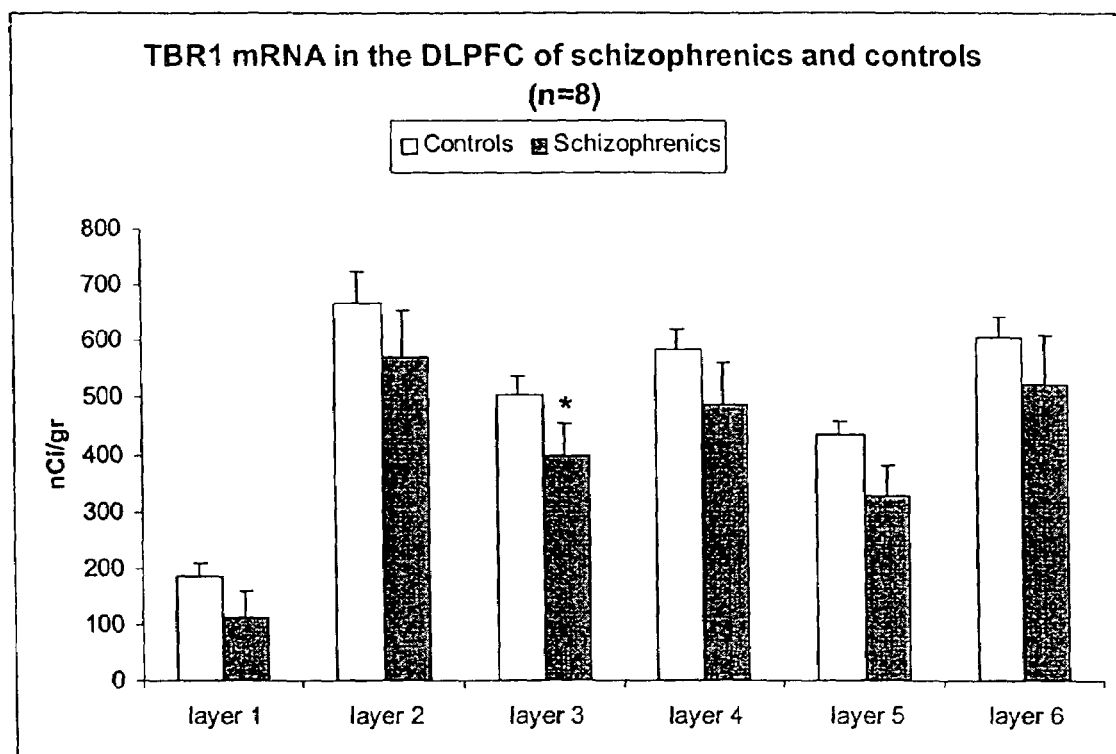
FIG. 7 shows TBR1 mRNA levels in the dorsolateral prefrontal cortex layers of schizophrenic patients. A trend toward reduction in TBR1 expression was found in all cortical layers in schizophrenics. This reduction was statistically significant in layer III.

As shown in FIG. 7, in general TBR1 mRNA expression tended to be decreased in the DLPFC of schizophrenic patients compared to controls. Statistical analysis of TBR1 expression using repeated measures analysis of variance (RMANOVA), revealed that the mean density of TBR1 mRNA was decreased in all layers (ANOVA F (1,84)=8.725, P<0.005). Two tailed paired t-test analysis on individual layers showed that the decrease was statistically significant in layer III (21% decrease; p=0.03; FIG. 7).

Discussion

The present study demonstrates that TBR1 is expressed in the DLPFC of adult human brain, and that there is a trend toward a reduction of TBR1 mRNA expression in all layers of the DLPFC of schizophrenic patients. The decrease was statistically significant in layer III, suggesting that pyramidal neurons of this middle layer which are the principal sources of cortico-cortical and commisural connections, are preferentially affected.

TBR1 is a transcription factor belonging to the family of the T-box genes, mainly expressed in glutamatergic cortical neurons during early development and associated with the development of cortical cytoarchitecture and connectivity (Hevner et al., 2001). In rodents it is expressed more widely during adult life, but its functional role in the adult brain remains to be clarified.

In the present study we report that TBR1 is also found in neurons from postmortem DLPFC of adult human subjects, and more highly expressed in layers IV and VI. In contrast, in one study (Hevner et al., 2001) in rodents TBR1 mRNA was reportedly more highly expressed in layers III and VI, although no data was shown; in fact, evidence for TBR1 expression exists for rodents only at postnatal day 0 (Bulfone et al., 1999; FIG. 2H) when layer IV is still not completely developed. Whether these differences between human and rodent TBR1 expression is a regional or a species-specific phenomenon has still to be investigated.

In our schizophrenic patients, we observed a general reduction of expression of TBR1 mRNA and in layer III, the measured decrease compared to normal controls was in the range of 20%. A reduction of the intensity of the hybridization signal in the cortex can be due to a decrease in the number of cells expressing TBR1 mRNA or to a decrease in the overall level of expression by individual cells. Prior studies have reported normal numbers of neurons (Pakkenberg, 1993; Akbarian et al., 1995), in the DLPFC of schizophrenic patients, and therefore our data are consistent with the hypothesis that there is less TBR1 mRNA per neuron in the DLPFC of patients with schizophrenia.

We quantified TBR1 mRNA expression using densitometry, a technique that measures the intensity of the signal/area irrespective of cell density in that area. Using this method, the intensity of the signal might vary because of variation in the cell density: for example more densely packed cells might elicit an increased hybridization signal. In the DLPFC of schizophrenic patients, cell density has been reported to be increased as a consequence of loss of neuropil (Selemon et al., 1998). Despite this, we still observed a decrease in the hybridization signal. This suggest that perhaps, at a single cell level, the reduction of TBR1 mRNA expression in cortical glutamatergic cells might be higher in magnitude than that we measured.

During development, TBR1 is associated with the migration of cortical neurons and the formation of appropriate synaptic connections. It is unknown whether TBR1 has a role in the maintenance of these connections in the adult cortex, and we cannot determine if TBR1 mRNA expression was reduced during the development of the cortex in our schizophrenic patients. However, abnormal expression of a transcription factor involved in the organization of cortico-cortical, cortico-thalamic and other subcortical circuitry during development, could lead to abnormalities of these circuits in adulthood. Since the greatest downregulation of TBR1 expression was in layer III, whose neurons reach the cortical plate during a defined developmental time window, a developmental disturbance acting on TBR1 could be highly restricted temporally.

Two independent in vitro studies demonstrated that TBR1 is involved in the regulation of expression of reelin, a polypeptide involved in the development of cortical lamination (Chen et al., 2002; Huesh et al., 2000). In particular, a site for Tbr-1 recognition has been demonstrated on the promoter of the human reelin gene, and it has been shown that Tbr-1 transfection in neuronal cell lines activates reelin expression (Chen et al., 2002). Reelin is an extracellular matrix protein that is expressed in the developing brain and continues to be expressed during the lifespan in a subpopulation of adult GABA-ergic neurons (Rice et al., 2001). It has been demonstrated that reelin mRNA and protein levels are reduced by 50% in cortical regions of patients with schizophrenia (Costa et al., 2001). Since reelin is synthesized by GABA-ergic cortical neurons, and TBR1 is mainly expressed in glutamatergic neurons, it is not clear whether the decrease in reelin expression in schizophrenia is a consequence of the reduction in TBR1 expression.

Finally, it is interesting to note that in the previous example we reported an abnormal expression of TBR1 mRNA in the DLPFC of bipolar patients, suggesting a more general involvement of this transcription factor in mental illnesses (Molnar et al., 2002). However, TBR1 mRNA expression was upregulated in the DLPFC of bipolar patients, suggesting that despite the similar symptoms shared by the two diseases, there are differences at the level of expression of specific molecular markers.

References

Akbarian, S., Sucher, N. J., Bradley, D., Tafazzoli, A., Trinh, D., Hetrick, W. P., Potkin, S. G., Sandman, C. A., Bunney, W. E., Jones, E. G. (1996a) Selective alterations in gene expression for NMDA receptor subunits in prefrontal cortex of schizophrenics. *J. Neurosci.* 16(1), 19-30.

Akbarian, S., Kim, J. J., Potkin, S. G., Hetrick, W. P., Bunney, W. E. jr., Jones, E. G. (1996b) Maldistribution of interstitial neurons in prefrontal white matter of the brains of schizophrenic patients. *Arch. Gen. Psychiatry* 53,425-436.

Akbarian, S., Kim, J. J., Potkin, S. G., Hagman, J. O., Tafazzoli, A., Bunney, W. E., Jones, E. G. (1995) Gene expression for glutamic acid decarboxylase is reduced without loss of neurons in prefrontal cortex of schizophrenics. *Arch. Gen. Psychiatry* 52, 258-266.

Andreasen, N. C., Rezai K., Alliger, R., Swayze, V. W., Flaum, M., Kirchner, P., Cohen, G., O'Leary, D. S. (1992) Hypofrontality in neuroleptic-naïve patients and in patients with chronic schizophrenia: assessment with xenon 133 single-photon emission computed tomography and the tower of London. *Arch. Gen. Psychiatry* 49, 943-958.

Buchsbaum, M. S., Haier, R. J., Potkin, S. G., Nuechterlein, K., Bracha, H. S., Katz, M., Lohr, J Wu, J., Lottnberg, S., Jerabek, P. A. (1992) Frontostriatal disorder of cerebral metabolism in never-medicated schizophrenics. *Arch. Gen. Psychiatry* 49, 935-942.

Bulfone, A., Martinez, S., Marigo, V., Campanella, M., Basile, A., Quaderi, N., Gattuso, C., Rubenstein, J. L. R., Ballabio, A. (1999) Expression pattern of the Thr2 (Eomesodermin) gene during mouse and chick brain development. *Mech Develop.* 84,133-138.

Bulfone, A., Smiga, S. M., Shimamura, K., Peterson, A., Puelles, L., Rubenstein, J. L. R. (1995) T-brain-1: a homolog of brachyury whose expression defines molecularly distinct domains within the cerebral cortex. *Neuron* 15,63-78.

Costa, E., Davis, J., Grayson, D. R., Guidotti, A., Pappas, G. D., Pesold, C. (2001) Dendritic spine hypoplasia and downregulation of reelin and GABA-ergic tone in schizophrenia vulnerability. *Neurobiol Dis.* 8, 723-742.

Dwyer, N. D., O'Leary, D. D. M. (2001) Tbr-1 conducts the orchestration of early cortical development. *Neuron* 29,309-319.

Glantz, L. A., Lewis, D. A. (2000) Decreased dendritic spine density on prefrontal cortical neurons in schizophrenia. *Arch. Gen. Psychiatry* 57, 65-73

Harrison, P. J. (1999) The neuropathology of schizophrenia: a critical review of data and their interpretation. *Brain* 122, 593-624.

Hazlett, E. A., Buchsbaum, M. S., Jeu, L. A., Nenadic, I., Fleischman, M. B., Shihabuddin, L., Haznedar, M. M., Harvey, P. D. (2000) Hypofrontality in unmedicated schizophrenia patients studied with PET during performance of a series of a verbal learning task. *Schizophr. Res.* 43, 33-46.

Hevner, R. F., Shi, L., Justice, N., Hsuesh, Y-P., Sheng, M., Smiga, S., Bulfone, A., Goffinet, A. M., Campagnoni, A. T., Rubenstein, J. L. R. (2001) Thr-1 regulates differentiation of the preplate and layer 6. *Neuron* 29,353-366.

Honer, W. G., Falkai, P., Chen, C., Arango, V., Mann, J. J., Dwork, A. J. (1999) Synaptic and plasticity associated proteins in anterior frontal cortex in severe mental illness. *Neurosci.* 91, 1247-1255

Huntsman, M. M., Tran, B. V., Potkin, S. G., Bunney, W. E., Jones, E. G. (1998) Altered ratio of alternatively spliced long and short γ 2 subunit mRNAs of the γ-amino butyrate type A receptor in prefrontal cortex of schizophrenics. *Proc Natl Acad Sci USA* 95,15066-15071.

Jones, E. G. (1997) Cortical development and thalamic development of schizophrenia. *Schizophr. Bull.*, 19, 431-445.

Jones, E. G., Hendry, S. H. C., Liu, X. B., Potkin, S. G., Tourtellotte, W. W. (1992) A method for fixation of previously fresh frozen human adult and fetal brains that preserves histological quality and immunoreactivity. *J Neurosci. Methods* 44,133-144.

Karson, C. N., Mrak, R. E., Schulterman, K. O., Sturner, W. Q., Sheng, J. G., Griffin W S (1999) Alterations in synaptic proteins and their encoding mRNAs in prefrontal cortex in schizophrenia: a possible neurochemical basis for 'hypofrontality'. *Mol Psychiatry* 4,39-45.

Lewis, D. A., Levitt, P., (2002) Schizophrenia as a disorder of neurodevelopment. *Ann. Rev. Neurosci.* 25,409-432.

Lewis, A. L., Pierri, J. N., Volk, D. W., Melchitzky, D. S., Woo, T-U. W. (1999) Altered GABA neurotransmission and prefrontal cortical dysfunction in schizophrenia. *Biol. Psychiatry* 46:616-626.

Molnar, M., Potkin, S. G., Bunney, W. E. jr., Jones E. G. (2002) mRNA expression pattern and distribution of white matter neurons in dorsolateral prefrontal cortex of depressed patients differ from those in schizophrenia. *Biol. Psychiatry.*

Pakkenberg, B. (1993) Total nerve cell number in neocortex in chronic schizophrenic and controls estimated using optical dissector. *Biol. Psychiatry* 34(11),768-772.

Pearlson G. D., Marsh, L. (1999) Structural imaging in schizophrenia: a selective review. *Biol. Psychiatry* 46,627-649.

Rice, D. S., Curran, T. (2001) Role of reelin signaling pathway in central nervous system development. *Annu. Rev. Neurosci.* 24, 1005-1039.

Selemon, L. D., Goldman-Rakic P (1999) The reduced neuropil hypothesis: a circuit based model of schizophrenia. *Biol. Psychiatry,* 45, 17-25.

Thompson, P. M., Sower, A. C., Perrone-Bizzozero, N. I. (1998) Altered levels of the synaptosomal associated protein SNAP-25 in schizophrenia. *Biol Psychiatry* 43,239-43.

Weickert, C. S., Webster, M. J., Hyde, T. M., Herman, M. M., Bachus, S. E., Balr, G., Weinberger, D. R., Kleinman, J. E. (2001) Reduced GAP-43 mRNA in dorsolateral prefrontal cortex of patients with schizophrenia. *Cereb. Cortex* 11,136-147.

Weinberger, D. R., Berman, K. F. (1996) Prefrontal function in schizophrenia: confounds and controversies. *Phil. R. Soc. Med.* 351, 1495-1503.

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A method for diagnosing bipolar disorder in a subject, the method comprising the steps of:
   (i) isolating a subject's brain tissue, wherein said tissue is selected from the subject's dorsal lateral prefrontal cortex;
   (ii) contacting the subject's brain tissue with a nucleic acid probe that selectively associates with an mRNA encoded by a nucleic acid with 95% identity to the sequence of SEQ ID NO: 3;
   (iii) detecting the level of said nucleic acid probe that associates with said mRNA; and
   (iv) comparing the detected level of associated probe with a control, whereby if the detected level is significantly greater than the control, an increased likelihood that the subject has bipolar disorder is determined; and whereby, if the detected level is not significantly greater than the control, an increase in said likelihood is not determined by the method.

2. The method of claim 1, wherein the subject is deceased.

3. A method for diagnosing bipolar disorder in a subject, the method comprising the steps of:
   (i) isolating a subject's brain tissue, wherein said tissue is selected from the subject's dorsal lateral prefrontal cortex;
   (ii) contacting the subject's brain tissue with a nucleic acid probe that selectively associates with an mRNA encoded by a nucleic acid with 95% identity to the sequence of SEQ ID NO: 1;
   (iii) detecting the level of said nucleic acid probe that associates with said mRNA; and
   (iv) comparing the detected level of probe with a control, whereby if the detected level is significantly greater than the control, an increased likelihood that the subject has bipolar disorder is determined; and whereby, if the detected level is not significantly greater than the control, an increase in said likelihood is not determined by the method.

4. The method of claim 3, wherein the subject is deceased.

5. The method of claim 1 or 3, wherein an increased likelihood of bipolar disorder is determined, and further comprising treating said subject for bipolar disorder following said determination.

* * * * *

```
                       SEQUENCE LISTING

<160> NUMBER OF SEQ ID NOS: 7

<210> SEQ ID NO 1
<211> LENGTH: 1495
<212> TYPE: DNA
<213> ORGANISM: Homo sapiens
<220> FEATURE:
<223> OTHER INFORMATION: calcium/calmodulin dependent protein kinase II
                        alpha-B subunit (CAMKII-alpha) cDNA
<220> FEATURE:
<221> NAME/KEY: CDS
<222> LOCATION: (7)..(1476)
<223> OTHER INFORMATION: CAMKII-alpha
<220> FEATURE:
<221> NAME/KEY: misc_feature
<222> LOCATION: (874)..(1223)
<223> OTHER INFORMATION: CAMKII-alpha riboprobe sequence

<400> SEQUENCE: 1
ttcaggatgg ctaccatcac ctgcacccgc ttcacggaag agtaccagct cttcgaggaa        60
ttgggcaagg gagccttctc ggtggtgcga aggtgtgtga aggtgctggc tggccaggag       120
tatgctgcca agatcatcaa cacaaagaag ctgtcagcca gagaccatca gaagctggag       180
cgtgaagccc gcatctgccg cctgctgaag cacccaaca tcgtccgact acatgacagc       240
atctcagagg agggacacca ctacctgatc ttcgacctgg tcactggtgg ggaactgttt       300
gaagatatcg tggcccggga gtattacagt gaggcggatg ccagtcactg tatccagcag       360
atcctggagg ctgtgctgca ctgccaccag atgggggtgg tgcaccggga cctgaagcct       420
gagaatctgt tgctggcctc caagctcaag ggtgccgcag tgaagctggc agactttggc       480
ctggccatag aggtggaggg ggagcagcag gcatggtttg ggtttgcagg gactcctgga       540
tatctctccc cagaagtgct gcggaaggac ccgtacggga agcctgtgga cctgtgggct       600
tgtggggtca tcctgtacat cctgctggtt gggtacccc cgttctggga tgaggaccag       660
```

-continued

```
caccgcctgt accagcagat caaagccggc gcctatgatt tcccatcgcc ggaatgggac    720
actgtcaccc cggaagccaa ggatctgatc aataagatgc tgaccattaa cccatccaaa    780
cgcatcacag ctgccgaagc ccttaagcac ccctggatct cgcaccgctc accgtggca     840 tcctgcatgc acagacagga gaccgtggac tgcctgaaga agttcaatgc caggaggaaa    900
ctgaagggag ccattctcac cacgatgctg gccaccagga acttctccgg agggaagagt    960
gggggaaaca gaagagcga tggtgtgaag aaaagaaagt ccagttccag cgttcagtta   1020
atggaatcct cagagagcac caacaccacc atcgaggatg aagacaccaa agtgcggaaa   1080
caggaaatta taaagtgac agagcagctg attgaagcca taagcaatgg aggttttgag     1140
tcctacacga agatgtgcga ccctggcatg acagccttcg aacctgaggc cctggggaac   1200
ctggttgagg gcctggactt ccatcgattc tattttgaaa acctgtggtc ccggaacagc   1260
aagcccgtgc acaccaccat cctgaatccc cacatccacc tgatgggcga cgagtcagcc   1320
tgcatcgcct acatccgcat cacgcagtac ctggacgctg gcggcatccc acgcaccgcc   1380
cagtcggagg agacccgtgt ctggcaccgc cgggacggca atggcagat cgtccacttc    1440 cacagatctg gggcgccctc cgtcctgccc cattgaagga ccaggccagg gtcaa         1495
```

<210> SEQ ID NO 2
<211> LENGTH: 489
<212> TYPE: PRT
<213> ORGANISM: Homo sapiens
<220> FEATURE:
<223> OTHER INFORMATION: calcium/calmodulin dependent protein kinase II
      alpha-B subunit (CAMKII-alpha)

<400> SEQUENCE: 2

```
Met Ala Thr Ile Thr Cys Thr Arg Phe Thr Glu Glu Tyr Gln Leu Phe
  1               5                  10                  15

Glu Glu Leu Gly Lys Gly Ala Phe Ser Val Val Arg Arg Cys Val Lys
                 20                  25                  30

Val Leu Ala Gly Gln Glu Tyr Ala Ala Lys Ile Ile Asn Thr Lys Lys
             35                  40                  45

Leu Ser Ala Arg Asp His Gln Lys Leu Glu Arg Glu Ala Arg Ile Cys
         50                  55                  60

Arg Leu Leu Lys His Pro Asn Ile Val Arg Leu His Asp Ser Ile Ser
 65                  70                  75                  80

Glu Glu Gly His His Tyr Leu Ile Phe Asp Leu Val Thr Gly Gly Glu
                 85                  90                  95

Leu Phe Glu Asp Ile Val Ala Arg Glu Tyr Tyr Ser Glu Ala Asp Ala
                100                 105                 110

Ser His Cys Ile Gln Gln Ile Leu Glu Ala Val Leu His Cys His Gln
            115                 120                 125

Met Gly Val Val His Arg Asp Leu Lys Pro Glu Asn Leu Leu Leu Ala
        130                 135                 140

Ser Lys Leu Lys Gly Ala Ala Val Lys Leu Ala Asp Phe Gly Leu Ala
145                 150                 155                 160

Ile Glu Val Glu Gly Glu Gln Gln Ala Trp Phe Gly Phe Ala Gly Thr
                165                 170                 175

Pro Gly Tyr Leu Ser Pro Glu Val Leu Arg Lys Asp Pro Tyr Gly Lys
            180                 185                 190

Pro Val Asp Leu Trp Ala Cys Gly Val Ile Leu Tyr Ile Leu Leu Val
        195                 200                 205
```

| | | | | | | | | | | | | | |
|---|---|---|---|---|---|---|---|---|---|---|---|---|---|
|Gly|Tyr|Pro|Pro|Phe|Trp|Asp|Glu|Asp|Gln|His|Arg|Leu|Tyr|Gln|Gln|
| |210| | | |215| | | |220| | | |

Ile Lys Ala Gly Ala Tyr Asp Phe Pro Ser Pro Glu Trp Asp Thr Val
225                 230                 235                 240

Thr Pro Glu Ala Lys Asp Leu Ile Asn Lys Met Leu Thr Ile Asn Pro
                245                 250                 255

Ser Lys Arg Ile Thr Ala Ala Glu Ala Leu Lys His Pro Trp Ile Ser
            260                 265                 270

His Arg Ser Thr Val Ala Ser Cys Met His Arg Gln Glu Thr Val Asp
        275                 280                 285

Cys Leu Lys Lys Phe Asn Ala Arg Arg Lys Leu Lys Gly Ala Ile Leu
    290                 295                 300

Thr Thr Met Leu Ala Thr Arg Asn Phe Ser Gly Gly Lys Ser Gly Gly
305                 310                 315                 320

Asn Lys Lys Ser Asp Gly Val Lys Lys Arg Lys Ser Ser Ser Ser Val
                325                 330                 335

Gln Leu Met Glu Ser Ser Glu Ser Thr Asn Thr Thr Ile Glu Asp Glu
            340                 345                 350

Asp Thr Lys Val Arg Lys Gln Glu Ile Ile Lys Val Thr Glu Gln Leu
        355                 360                 365

Ile Glu Ala Ile Ser Asn Gly Gly Phe Glu Ser Tyr Thr Lys Met Cys
    370                 375                 380

Asp Pro Gly Met Thr Ala Phe Glu Pro Glu Ala Leu Gly Asn Leu Val
385                 390                 395                 400

Glu Gly Leu Asp Phe His Arg Phe Tyr Phe Glu Asn Leu Trp Ser Arg
                405                 410                 415

Asn Ser Lys Pro Val His Thr Thr Ile Leu Asn Pro His Ile His Leu
            420                 425                 430

Met Gly Asp Glu Ser Ala Cys Ile Ala Tyr Ile Arg Ile Thr Gln Tyr
        435                 440                 445

Leu Asp Ala Gly Gly Ile Pro Arg Thr Ala Gln Ser Glu Glu Thr Arg
    450                 455                 460

Val Trp His Arg Arg Asp Gly Lys Trp Gln Ile Val His Phe His Arg
465                 470                 475                 480

Ser Gly Ala Pro Ser Val Leu Pro His
                485

```
<210> SEQ ID NO 3
<211> LENGTH: 3186
<212> TYPE: DNA
<213> ORGANISM: Homo sapiens
<220> FEATURE:
<223> OTHER INFORMATION: T-brain-1 (TBR1) cDNA
<220> FEATURE:
<221> NAME/KEY: CDS
<222> LOCATION: (303)..(2351)
<223> OTHER INFORMATION: TBR1
<220> FEATURE:
<221> NAME/KEY: misc_feature
<222> LOCATION: (303)..(1438)
<223> OTHER INFORMATION: TBR1 riboprobe sequence

<400> SEQUENCE: 3
```

| | |
|---|---|
|caggtgatta tcctaattaa tgtctatcta attaaattac tgtcagcagc taaccaatgg|60|
|caggagccgt tcatcggct gcacaagcag caagatcaaa agtgagcctt ttctgattgc|120|
|tgcatagtgt caattggcca atctcttctc ccagggaaaa aaaaagtaa atcaaacctt|180|
|tgagaagcat tgctggttg aagtgctttc tgtctagtga gggggtctgt ggatttctag|240|

```
tttatgataa ataggacttt aaaaaccagg gacgggaggg cgagtgttca ggttctagag      300
ctatgcagct ggagcactgc ctttctcctt ctatcatgct ctccaagaaa tttctcaatg      360
tgagcagcag ctaccacat tcaggcggat ccgagcttgt cttgcacgat catcccatta       420
tctcgaccac tgacaacctg gagagaagtt cacctttgaa aaaaattacc aggggatga      480 cgaatcagtc agatacagac aattttcctg actccaagga ctcaccaggg gacgtccaga     540
gaagtaaact ctctcctgtc ttggacgggg tctctgagct tcgtcacagt ttcgatggct     600
ctgctgcaga tcgctacctc ctctctcagt ccagccagcc acagtctgcg gccactgctc    660
ccagtgccat gttcccgtac cccggccagc acggaccggc gcaccccgcc ttctccatcg     720
gcagccctag ccgctacatg gcccaccacc cggtcatcac caacggagcc tacaacagcc    780
tcctgtccaa ctcctcgccg cagggatacc ccacggccgg ctaccctac ccacagcagt     840 acggccactc ctaccaagga gctccgttct accagttctc ctccacccag ccggggctgg    900
tgcccggcaa agcacaggtg tacctgtgca caggccccct ttggctgaaa tttcaccggc    960
accaaacgga gatgatcatc accaaacagg aaggcgcat gttttccttt ttaagttta     1020 acatttctgg tctcgatccc acggctcatt acaatatttt tgtggatgtg attttggcgg   1080
atcccaatca ctggaggttt caaggaggca aatgggttcc ttgcggcaaa gcggacacca   1140
atgtgcaaga aaatcgggtc tatatgcatc cggattcccc caacactggg gctcactgga   1200
tgcgccaaga aatctctttt ggaaaattaa aacttacgaa caacaaagga gcttcaaata   1260
acaatgggca gatggtggtt ttacagtcct tgcacaagta ccagccccgc ctgcatgtgg   1320
tggaagtgaa cgaggacggc acggaggaca ctagccagcc cggccgcgtg cagacgttca   1380
cttcccctga gactcagttc atcgccgtca ccgcctacca gaacacggat attacacaac   1440
tgaaaataga tcacaaccct tttgcaaaag gatttcggga taattatgac acgatctaca   1500
ccggctgtga catggaccgc ctgacccct cgcccaacga ctcgccgcgc tcgcagatcg    1560
tgcccggggc ccgctacgcc atggccggct cttttcctgca ggaccagttc gtgagcaact   1620
acgccaaggc ccgcttccac ccgggcgcgg gcgcgggccc cgggccgggt acggaccgca   1680
gcgtgccgca caccaacggg ctgctgtcgc cgcagcaggc cgaggacccg ggcgcgccct   1740
cgccgcaacg ctggtttgtg acgccggcca acaccggct ggacttcgcg gcctcggcct    1800
atgacacggc cacggacttc gcgggcaacg cggccacgct gctctcttac gcggcggcgg   1860
gcgtgaaggc gctgccgctg caggctgcag gctgcactgg ccgcccgctc ggctactacg   1920
ccgacccgtc gggctggggc gcccgcagtc ccccgcagta ctgcggcacc aagtcgggct   1980
cggtgctgcc ctgctggccc aacagcgccg cggccgccgc gcgcatggcc ggcgccaatc   2040
cctacctggg cgaggaggcc gagggcctgg ccgccgagcg ctcgccgctg ccgcccggcg   2100
ccgccgagga cgccaagccc aaggacctgt ccgattccag ctggatcgag acgccctcct   2160
cgatcaagtc catcgactcc agcgactcgg ggatttacga gcaggccaag cggaggcgga   2220
tctcgccggc cgacacgccc gtgtccgaga ttcgtcccc gctcaagagc gaggtgctgg    2280
cccagcggga ctgcgagaag aactgcgcca aggacattag cggctactat ggcttctact   2340
cgcacagcta ggccgcccct gccgcccgg ccccgccgcg gccggacccc cagccagcc     2400 cctcacagct cttccccagc tccgcctccc cacactcctc cttgcgcacc cactcatttt   2460
atttgaccct cgatggccgt ctgcagcgaa taagtgcagg tctccgagcg tgattttaac   2520
cttttttgca cagcagtctc tgcaattagc tcaccgacct tcaactttgc tgtaaacctt   2580
ttggttttcc tacttactct tcttctgtgg agttatcctc ctacaattcc cctcccctc    2640
```

-continued

```
gtctttctct tacctcctac ttctctttct tgtaatgaaa ctcttcacct ttaggagacc      2700
tgggcagtcc tgtcaggcag cagcgattcc gacccgccaa gtctcggcct ccacattaac      2760
cataggatgt tgactctaga acctggaccc acccagcgcg tcctttctta tccccgagtg      2820
gatggatgga tggatggatg gtagggatgt taataatttt agtggaacaa agcctgtgaa      2880
atgattgtac atagtgttaa tttattgtaa cgaatggcta gtttttattc tcgtcaaggc      2940
acaaaaccag ttcatgctta accttttttt cctttccttt ctttgctttt ctttctctcc      3000
tctcatactt tctcttctct ctcttttaat tttcttgtga gataatattc taagaggctc      3060
tagaaacatg aaatactcag tagtgatggg tttcccactt ctcctcaatc cgttgcatga      3120 ataattact atgtgcccta atgcacacaa atagctaagg agaatccacc caaacacctt      3180
taaagg                                                                3186
```

<210> SEQ ID NO 4
<211> LENGTH: 682
<212> TYPE: PRT
<213> ORGANISM: Homo sapiens
<220> FEATURE:
<223> OTHER INFORMATION: T-brain-1 (TBR1)

<400> SEQUENCE: 4

```
Met Gln Leu Glu His Cys Leu Ser Pro Ser Ile Met Leu Ser Lys Lys
  1               5                  10                  15

Phe Leu Asn Val Ser Ser Ser Tyr Pro His Ser Gly Gly Ser Glu Leu
             20                  25                  30

Val Leu His Asp His Pro Ile Ile Ser Thr Thr Asp Asn Leu Glu Arg
         35                  40                  45

Ser Ser Pro Leu Lys Lys Ile Thr Arg Gly Met Thr Asn Gln Ser Asp
     50                  55                  60

Thr Asp Asn Phe Pro Asp Ser Lys Asp Ser Pro Gly Asp Val Gln Arg
 65                  70                  75                  80

Ser Lys Leu Ser Pro Val Leu Asp Gly Val Ser Glu Leu Arg His Ser
                 85                  90                  95

Phe Asp Gly Ser Ala Ala Asp Arg Tyr Leu Leu Ser Gln Ser Ser Gln
            100                 105                 110

Pro Gln Ser Ala Ala Thr Ala Pro Ser Ala Met Phe Pro Tyr Pro Gly
        115                 120                 125

Gln His Gly Pro Ala His Pro Ala Phe Ser Ile Gly Ser Pro Ser Arg
    130                 135                 140

Tyr Met Ala His His Pro Val Ile Thr Asn Gly Ala Tyr Asn Ser Leu
145                 150                 155                 160

Leu Ser Asn Ser Ser Pro Gln Gly Tyr Pro Thr Ala Gly Tyr Pro Tyr
                165                 170                 175

Pro Gln Gln Tyr Gly His Ser Tyr Gln Gly Ala Pro Phe Tyr Gln Phe
            180                 185                 190

Ser Ser Thr Gln Pro Gly Leu Val Pro Gly Lys Ala Gln Val Tyr Leu
        195                 200                 205

Cys Asn Arg Pro Leu Trp Leu Lys Phe His Arg His Gln Thr Glu Met
    210                 215                 220

Ile Ile Thr Lys Gln Gly Arg Arg Met Phe Pro Phe Leu Ser Phe Asn
225                 230                 235                 240

Ile Ser Gly Leu Asp Pro Thr Ala His Tyr Asn Ile Phe Val Asp Val
                245                 250                 255
```

```
Ile Leu Ala Asp Pro Asn His Trp Arg Phe Gln Gly Gly Lys Trp Val
            260                 265                 270

Pro Cys Gly Lys Ala Asp Thr Asn Val Gln Gly Asn Arg Val Tyr Met
        275                 280                 285

His Pro Asp Ser Pro Asn Thr Gly Ala His Trp Met Arg Gln Glu Ile
    290                 295                 300

Ser Phe Gly Lys Leu Lys Leu Thr Asn Asn Lys Gly Ala Ser Asn Asn
305                 310                 315                 320

Asn Gly Gln Met Val Val Leu Gln Ser Leu His Lys Tyr Gln Pro Arg
                325                 330                 335

Leu His Val Val Glu Val Asn Glu Asp Gly Thr Glu Asp Thr Ser Gln
            340                 345                 350

Pro Gly Arg Val Gln Thr Phe Thr Phe Pro Glu Thr Gln Phe Ile Ala
        355                 360                 365

Val Thr Ala Tyr Gln Asn Thr Asp Ile Thr Gln Leu Lys Ile Asp His
    370                 375                 380

Asn Pro Phe Ala Lys Gly Phe Arg Asp Asn Tyr Asp Thr Ile Tyr Thr
385                 390                 395                 400

Gly Cys Asp Met Asp Arg Leu Thr Pro Ser Pro Asn Asp Ser Pro Arg
                405                 410                 415

Ser Gln Ile Val Pro Gly Ala Arg Tyr Ala Met Ala Gly Ser Phe Leu
            420                 425                 430

Gln Asp Gln Phe Val Ser Asn Tyr Ala Lys Ala Arg Phe His Pro Gly
        435                 440                 445

Ala Gly Ala Gly Pro Gly Pro Gly Thr Asp Arg Ser Val Pro His Thr
    450                 455                 460

Asn Gly Leu Leu Ser Pro Gln Gln Ala Glu Asp Pro Gly Ala Pro Ser
465                 470                 475                 480

Pro Gln Arg Trp Phe Val Thr Pro Ala Asn Asn Arg Leu Asp Phe Ala
                485                 490                 495

Ala Ser Ala Tyr Asp Thr Ala Thr Asp Phe Ala Gly Asn Ala Ala Thr
            500                 505                 510

Leu Leu Ser Tyr Ala Ala Ala Gly Val Lys Ala Leu Pro Leu Gln Ala
        515                 520                 525

Ala Gly Cys Thr Gly Arg Pro Leu Gly Tyr Tyr Ala Asp Pro Ser Gly
    530                 535                 540

Trp Gly Ala Arg Ser Pro Pro Gln Tyr Cys Gly Thr Lys Ser Gly Ser
545                 550                 555                 560

Val Leu Pro Cys Trp Pro Asn Ser Ala Ala Ala Ala Arg Met Ala
                565                 570                 575

Gly Ala Asn Pro Tyr Leu Gly Glu Glu Ala Gly Leu Ala Ala Glu
            580                 585                 590

Arg Ser Pro Leu Pro Pro Gly Ala Ala Glu Asp Ala Lys Pro Lys Asp
        595                 600                 605

Leu Ser Asp Ser Ser Trp Ile Glu Thr Pro Ser Ser Ile Lys Ser Ile
    610                 615                 620

Asp Ser Ser Asp Ser Gly Ile Tyr Glu Gln Ala Lys Arg Arg Arg Ile
625                 630                 635                 640

Ser Pro Ala Asp Thr Pro Val Ser Glu Ser Ser Ser Pro Leu Lys Ser
                645                 650                 655
```

-continued

Glu Val Leu Ala Gln Arg Asp Cys Glu Lys Asn Cys Ala Lys Asp Ile
            660                 665                 670

Ser Gly Tyr Tyr Gly Phe Tyr Ser His Ser
        675                 680

<210> SEQ ID NO 5
<211> LENGTH: 1501
<212> TYPE: DNA
<213> ORGANISM: Homo sapiens
<220> FEATURE:
<223> OTHER INFORMATION: calcium/calmodulin dependent protein kinase I
      (CAMKI) cDNA
<220> FEATURE:
<221> NAME/KEY: CDS
<222> LOCATION: (179)..(1291)
<223> OTHER INFORMATION: CAMKI

<400> SEQUENCE: 5

```
ggagagagcc gccgagccga gccgagcccc agctccagca agagcgcggg cgggtggccc        60
aggcacgcag cggtgaggac gcggccaca  gctcggcgcc aaccaccgcg ggcctcccag       120
ccagccccgc ggcggggcag ccgcaggagc cctggctgtg gtcggggggc agtgggccat       180
gctgggggca gtggaaggcc ccaggtggaa gcaggcggag gacattagag acatctacga       240
cttccgagat gttctgggca cgggggcctt ctcggaggtg atcctggcag aagataagag       300
gacgcagaag ctggtggcca tcaaatgcat tgccaaggag gccctggagg caaggaagg        360
cagcatggag aatgagattg ctgtcctgca caagatcaag caccccaaca ttgtagccct       420
ggatgacatc tatgagagtg ggggccacct ctacctcatc atgcagctgg tgtcgggtgg       480
ggagctcttt gaccgtattg tggaaaaagg cttctacacg gagcgggacg ccagccgcct       540
catcttccag gtgctggatg ctgtgaaata cctgcatgac ctgggcattg tacaccggga       600
tctcaagcca gagaatctgc tgtactacag cctggatgaa gactccaaaa tcatgatctc       660
cgactttggc ctctccaaga tggaggaccc gggcagtgtg ctctccaccg cctgtggaac       720
tccgggatac gtggcccctg aagtcctggc ccagaagccc tacagcaagg ctgtggattg       780
ctggtccata ggtgtcatcg cctacatctt gctctgcggt taccctccct tctatgacga       840
gaatgatgcc aaactctttg aacagatttt gaaggccgag tacgagtttg actctcctta       900
ctgggacgac atctctgact ctgccaaaga tttcatccgg cacttgatgg agaaggaccc       960
agagaaaaga ttcacctgtg agcaggcctt gcagcaccca tggattgcag agatacagc       1020
tctagataag aatatccacc agtcggtgag tgagcagatc aagaagaact ttgccaagag      1080
caagtggaag caagccttca tgccacggc tgtggtgcgg cacatgagga aactgcagct      1140
gggcaccagc caggaggggc aggggcagac ggcgagccat ggggagctgc tgacaccagt      1200
ggctgggggg ccggcagctg ctgttgctg  tcgagactgc tgcgtggagc cgggcacaga      1260
actgtccccc acactgcccc accagctcta gggccctgga cctcgggtca tgatcctctg      1320
cgtgggaggg cttgggggca gcctgctccc cttccctccc tgaaccggga gtttctctgc      1380
cctgtcccct cctcacctgc ttccctacca ctcctcactg cattttccat acaaatgttt      1440
ctattttatt gttccttctt gtaataaagg gaagataaaa ccaaaaaaaa aaaaaaaaaa      1500
a                                                                     1501
```

<210> SEQ ID NO 6
<211> LENGTH: 370
<212> TYPE: PRT
<213> ORGANISM: Homo sapiens

```
<220> FEATURE:
<223> OTHER INFORMATION: calcium/calmodulin dependent protein kinase I
      (CAMKI)

<400> SEQUENCE: 6

Met Leu Gly Ala Val Glu Gly Pro Arg Trp Lys Gln Ala Glu Asp Ile
 1               5                  10                  15

Arg Asp Ile Tyr Asp Phe Arg Asp Val Leu Gly Thr Gly Ala Phe Ser
                20                  25                  30

Glu Val Ile Leu Ala Glu Asp Lys Arg Thr Gln Lys Leu Val Ala Ile
            35                  40                  45

Lys Cys Ile Ala Lys Glu Ala Leu Glu Gly Lys Glu Gly Ser Met Glu
        50                  55                  60

Asn Glu Ile Ala Val Leu His Lys Ile Lys His Pro Asn Ile Val Ala
 65                  70                  75                  80

Leu Asp Asp Ile Tyr Glu Ser Gly Gly His Leu Tyr Leu Ile Met Gln
                85                  90                  95

Leu Val Ser Gly Gly Glu Leu Phe Asp Arg Ile Val Glu Lys Gly Phe
            100                 105                 110

Tyr Thr Glu Arg Asp Ala Ser Arg Leu Ile Phe Gln Val Leu Asp Ala
        115                 120                 125

Val Lys Tyr Leu His Asp Leu Gly Ile Val His Arg Asp Leu Lys Pro
    130                 135                 140

Glu Asn Leu Leu Tyr Tyr Ser Leu Asp Glu Asp Ser Lys Ile Met Ile
145                 150                 155                 160

Ser Asp Phe Gly Leu Ser Lys Met Glu Asp Pro Gly Ser Val Leu Ser
                165                 170                 175

Thr Ala Cys Gly Thr Pro Gly Tyr Val Ala Pro Glu Val Leu Ala Gln
            180                 185                 190

Lys Pro Tyr Ser Lys Ala Val Asp Cys Trp Ser Ile Gly Val Ile Ala
        195                 200                 205

Tyr Ile Leu Leu Cys Gly Tyr Pro Pro Phe Tyr Asp Glu Asn Asp Ala
    210                 215                 220

Lys Leu Phe Glu Gln Ile Leu Lys Ala Glu Tyr Glu Phe Asp Ser Pro
225                 230                 235                 240

Tyr Trp Asp Asp Ile Ser Asp Ser Ala Lys Asp Phe Ile Arg His Leu
                245                 250                 255

Met Glu Lys Asp Pro Glu Lys Arg Phe Thr Cys Glu Gln Ala Leu Gln
            260                 265                 270

His Pro Trp Ile Ala Gly Asp Thr Ala Leu Asp Lys Asn Ile His Gln
        275                 280                 285

Ser Val Ser Glu Gln Ile Lys Lys Asn Phe Ala Lys Ser Lys Trp Lys
    290                 295                 300

Gln Ala Phe Asn Ala Thr Ala Val Val Arg His Met Arg Lys Leu Gln
305                 310                 315                 320

Leu Gly Thr Ser Gln Glu Gly Gln Gly Gln Thr Ala Ser His Gly Glu
                325                 330                 335

Leu Leu Thr Pro Val Ala Gly Gly Pro Ala Ala Gly Cys Cys Cys Arg
            340                 345                 350

Asp Cys Cys Val Glu Pro Gly Thr Glu Leu Ser Pro Thr Leu Pro His
        355                 360                 365

Gln Leu
    370
```

```
<210> SEQ ID NO 7
<211> LENGTH: 200
<212> TYPE: PRT
<213> ORGANISM: Artificial Sequence
<220> FEATURE:
<223> OTHER INFORMATION: Description of Artificial Sequence:poly-Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 7

Gly Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
             85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly Gly
        180                 185                 190

Gly Gly Gly Gly Gly Gly Gly Gly
    195                 200
```